United States Patent
Redei et al.

(10) Patent No.: US 6,348,571 B1
(45) Date of Patent: Feb. 19, 2002

(54) CORTICOTROPIN RELEASE INHIBITING FACTOR AND METHODS OF USING SAME

(75) Inventors: Eva Redei, Chicago; Fraser Aird, Oak Park, both of IL (US)

(73) Assignees: Northwestern University, Evanston, IL (US); The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 09/366,627

(22) Filed: Aug. 3, 1999

Related U.S. Application Data

(63) Continuation-in-part of application No. 08/660,561, filed on Jun. 7, 1996, now Pat. No. 6,039,956, which is a continuation-in-part of application No. 08/523,125, filed on Sep. 8, 1995, now Pat. No. 5,830,866, which is a continuation-in-part of application No. 08/304,383, filed on Sep. 12, 1994, now abandoned.

(51) Int. Cl.$^7$ .............. C07K 4/12; C07K 5/00; C07K 7/06; C07K 7/08; C07K 14/435

(52) U.S. Cl. .............. 530/330; 530/324; 530/325; 530/326; 530/327

(58) Field of Search .............. 514/13, 14, 15, 514/16, 17, 18; 530/326, 327, 328, 329, 330, 331, 324, 325; 424/198.1

(56) References Cited

U.S. PATENT DOCUMENTS

| | | | |
|---|---|---|---|
| 4,160,452 A | | 7/1979 | Theeuwes |
| 4,256,108 A | | 3/1981 | Theeuwes |
| 4,265,874 A | | 5/1981 | Bonsen et al. |
| 5,334,702 A | | 8/1994 | Greene et al. |
| 5,830,866 A | * | 11/1998 | Redei et al. ............. 514/18 |
| 6,039,956 A | * | 3/2000 | Redei et al. ............. 424/198.1 |

OTHER PUBLICATIONS

Bulant et al. J Biol Chem. Nov. 15, 1988; 263(32):17189–96.*
Satoh et al. Cloning of the mouse hypothalamic preprothyrotropin–releasing hormone (TRH) cDNA and tissue distribution of its mRNA. Brain Res Mol Brain Res. Jun. 14, 1992; (1–2):131–5.*
Bowie et al. Deciphering the message in protein sequences: tolerance to amino acid substitutions. Science, (Mar. 16, 1990) 247 (4948) 1306–10.*
Ngo et al., in The Protein Folding Problem and Tertiary Structure Prediction, Merz and Le Grand (Eds), Aug. 1994, Springer Verlag, pp. 433 and 492–495, Sep. 1994.*
Bird et al., 1988, Science 42:423–426.
Grossman and Tsagarakis, 1989, J. Endocrinology 123:169–172.
Huston et al., 1988, Proc. Natl. Acad. Sci. USA 85:5879–5883.
Kakucska et al., 1992, Endocrinology 130:2845–2850.
Karalis et al., 1991, Science 254:421.
Lechan et al., 1986, Science 231:159–161.
Lee et al., 1988, J. Biol. Chem. 263:16604–16609.
McGivern et al., 1997, J. Neurosci. 17:4886–4894.
Nillni et al., 1993, endocrinology 132:1260–1270.
Palermo et al., 1994, Acta Eur. Fertilitatis 25:161–172.
Pare and Redei, 1993, J. Physiol. 87:229–238.
Plotsky, 1991, J. Neuroendocrinol. 3:1–9.
Prystowsky et al., 1994, Immunomethods 5:49–55.
Redei and Endroczi, 1984, IN: Integrative Neurohormonal Mechanism Developments in Neuroscience, Endroczi et al., Eds. Elsevier, Amsterdam, 377–383.
Redei et al., 1989, IN: Neuropeptides and Stress, Tache et al., Eds. Springer–Verlag, NY, 6:62–72.
Redei et al., 1988, Endocrinology, 123:2736–2743.
Redei et al., 1993, Endocrinology 133:452–460.
Redei et al., 1994, Am. J. Physiol. 266:R353–R360.
Redei et al., 1994, Neuroendocrinology 60:113–123.
Sabol, 1980, Arch. Biochem. Biophys. 203:37–48.
Segerson et al., 1987, Science 238:78.
Sevarino et al., 1989, J. Biol. Chem. 264:215229–215235.
Silman, 1994, APMIS 102:721–728.
Sternberg et al., 1989, Proc. Natl. Acad. Sci. USA 86:2374–2378.
Uhler et al., 1983, J. Biol. Chem. 258:257–261.
Walker et al., 1995, Lupus 4:3–9.
Yamada et al., 1990, Molec. Endocrinol. 4:551–557.
Zumoff, 1994, Ob. & Gyn. Clinics of N. Am. 21:751–772.

* cited by examiner

*Primary Examiner*—David S. Romeo
(74) *Attorney, Agent, or Firm*—Morgan, Lewis & Bockius, L.L.P.

(57) ABSTRACT

The invention includes a substantially pure preparation of a corticotropin release inhibiting factor (CRIF) peptide having from three to twenty one or to twenty five contiguous amino acids contained within the amino acid sequence positioned between the fourth and fifth TRH sequence on a prepro-TRH protein.

2 Claims, 26 Drawing Sheets

Basal
| Control | pCMV-TRH | ΔApa I | ΔBstE II |
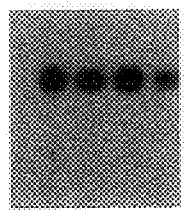
50 nM CRF
| Control | pCMV-TRH | ΔApa I | ΔBstE II |
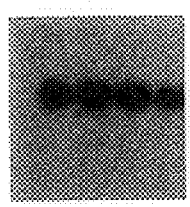
Fig. 4B

Amino Acid Sequence

RatCRIF

FIG. 10

Prepro rat TRH 178-199

Phe-Ile-Asp-Pro-Glu-Leu-Gln-Arg-Ser-Trp-Glu-Glu-Lys-Glu-Gly-Glu-Gly-Val-Leu-Met-Pro-Glu

Prepro rat TRH 172-199 (including 3 amino acids of TRH-pGlu-His-Pro)

pGlu-His-Pro-Gly-Arg-Arg-.....(prepro-TRH 178-199)

Human corresponding sequences:

Prepro human TRH 158-183; 53.8% homology with the rat CRIF sequence

Leu-Ala-Asp-Pro-Lys-Ala-Gln-Arg-Ser-Trp-Glu-Glu-Glu-Glu-Glu-Glu-Glu-Arg-Glu-Glu-Asp-Leu-Met-Pro-Glu

Possible uncleaved TRH: prepro-human TRH 152-183 pGlu-His-Pro-Gly-Arg-Arg-.....(prepro-human TRH 158-183)

Mouse corresponding sequences:

Prepro-mouse TRH 178-200; 87% homology with the rat CRIF sequence

Phe-Ile-Asp-Pro-Glu-Leu-Gln-Arg-Ser-Trp-Glu-Glu-Thr-Glu-Gly-Glu-Glu-Gly-Gly-Leu-Met-Pro-Glu

Possible uncleaved TRH: prepro mouse TRH 172-200 pGlu-His-Pro-Gly-Arg-Arg-.....(prepro-mouse TRH 178-200)

DNA Sequence

Rat: 172-199

CAACATCCAGGCCGGAGGTTCATAGATCCCGAGCTCCAAAGAAGCTGGGAAG
AAAAAGAGGGAGAGGGTGTCTTAATGCCTGAG

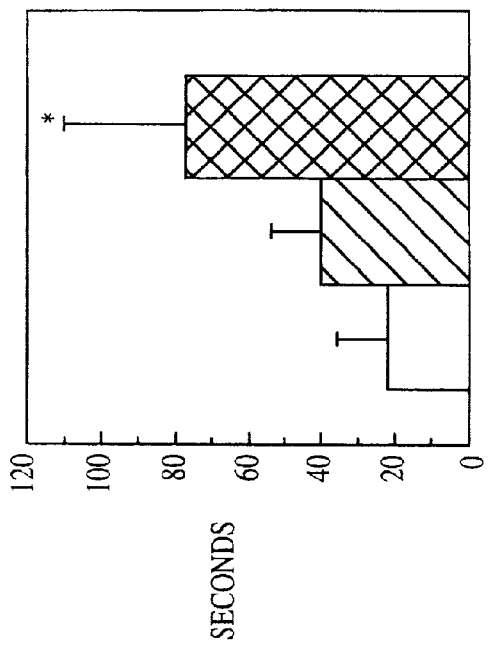
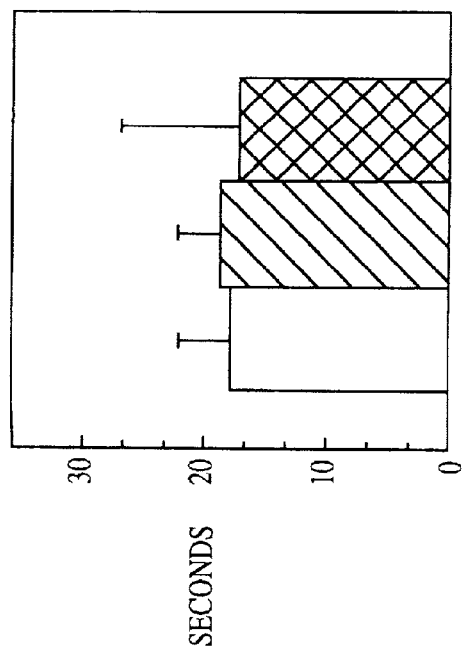
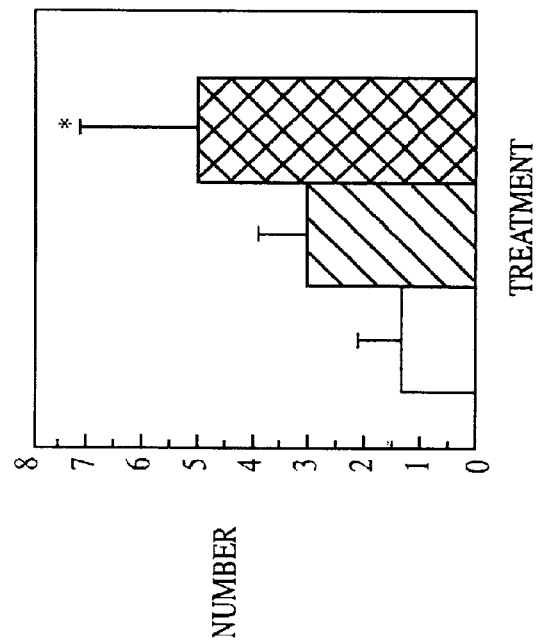
FIG. 17A
FIG. 17B
FIG. 17C

| RAT PREPRO-TRH 178-199 | FIDPELQRSWEEKEGEGVLMPE |
| RAT PREPRO-TRH 191-199 | EGEGVLMPE |
| RAT PREPRO-TRH 196-199 | LMPE |

US 6,348,571 B1

CORTICOTROPIN RELEASE INHIBITING FACTOR AND METHODS OF USING SAME

CROSS REFERENCE TO RELATED APPLICATIONS

This is a continuation-in-part of U.S. application Ser. No. 08/660,561, filed on Jun. 7, 1996 now U.S. Pat. No. 6,039,956, which is a continuation-in-part of application Ser. No. 08/523,125, filed on Sep. 8, 1995, now issued U.S. Pat. No. 5,830,866, which is a continuation-in-part of application Ser. No. 08/304,383, filed on Sep. 12, 1994 now abandoned.

STATEMENT OF FEDERALLY SPONSORED RESEARCH SUPPORT AND DEVELOPMENT

This invention was supported in part by funds from the U.S. Government (NIAAA 06478) and the U.S. Government may have certain rights in the invention.

BACKGROUND OF THE INVENTION

The onset and/or severity of illness in mammals is related to the level of stress experienced by that mammal. In patients who are ill, either hypo- or hyperactivity of the hypothalamic-pituitary-adrenocortical (HPA) axis has been observed, which activity represents the physiological regulator of the stress response in mammals.

Regulation of HPA occurs via a multifaceted integrated mechanism, wherein corticotropin-releasing factor (CRF) and vasopressin (AVP) produced by the brain are believed to stimulate production of adrenocortico-tropin (ACTH) from the anterior pituitary, the primary inducer of cortisol secretion. Cortisol so produced has a negative influence upon ACTH secretion thus providing a feedback regulatory mechanism within this system.

An additional ACTH-inhibiting factor is postulated by Grossman and Tsagarakis (1989, J. Endocrinology, 123:169–172), which is termed corticotropin release inhibiting factor (CRIF or CIF), see Redei et al., In: Neuropeptides and Stress, Eds. Tache et al., Hans Selye Symposia on Neuroendocrinology and Stress, 1989, Springer-Verlag, N.Y.). This activity comprises an unidentified hypothalamic peptide, which peptide exhibits inhibitory activity on basal and CRF or stress stimulated ACTH secretion both in vitro and in vivo (Redei et al., 1984, In: Integrative Neurohormonal Mechanism Developments in Neuroscience, Vol. 16, Eds. Endroczi et a, Elsevier, Amsterdam).

A hypothalamic peptide fraction isolated from both pigs and rats was found to contain CRIF activity. When injected into rats, it suppressed corticosterone (CORT) response to footshock (Redei et al., 1984, In: Integrative Neurohormonal Mechanism Developments in Neuroscience, Vol. 16, Eds. Endroczi et al, Elsevier, Amsterdam). In addition, a peptide fraction (molecular weight 0.6–2.3 kDa) has been isolated from bovine hypothalamus which exhibits CRIF activity both in vitro and in vivo (Redei et al., In: Neuropeptides and Stress, Eds. Tache et al., Hans Selye Symposia on Neuroendocrinology and Stress, 1989, Springer-Verlag, N.Y.).

There has been a long felt need to determine the identity of CRIF because of its important relationship in regulating ACTH production. The present invention satisfies this need.

SUMMARY OF THE INVENTION

The invention relates to a substantially pure preparation of a CRIF peptide consisting of from three to twenty one contiguous amino acids contained within the amino acid sequence positioned between the fourth and fifth TRH sequence on a prepro-TRH protein.

In one aspect the peptide consists of a contiguous length of amino acids selected from the group consisting of three, four, five, six, seven, eight, nine, ten, eleven, twelve, thirteen, fourteen, fifteen, sixteen, seventeen, eighteen, nineteen, twenty and twenty one amino acids.

In one embodiment, the peptide consists of four contiguous amino acids.

In another embodiment, the peptide has the sequence Leu-Met-Pro-Glu [SEQ ID NO:6].

In another embodiment, the peptide consists of nine contiguous amino acids.

In yet another embodiment, the peptide has the sequence Glu-Gly-Glu-Gly-Val-Leu-Met-Pro-Glu [SEQ ID NO:5].

In another aspect, the CRIF peptide is rat CRIF.

In one embodiment, the peptide consists of from three to twenty one contiguous amino acids of the sequence Phe-Ile-Asp-Pro-Glu-Leu-Gln-Arg-Ser-Trp-Glu-Glu-Lys-Glu-Gly-Glu-Gly-Val-Leu-Met-Pro-Glu [SEQ ID NO:1].

In another aspect, the CRIF peptide is mouse CRIF.

In one embodiment, the peptide consists of from three to twenty one contiguous amino acids of the sequence Phe-Ile-Asp-Pro-Glu-Leu-Gln-Arg-Ser-Trp-Glu-Glu-Thr-Glu-Gly-Glu-Gly-Gly-Gly-Leu-Met-Pro-Glu [SEQ ID NO:3].

In yet another aspect, the peptide is in a pharmaceutically acceptable carrier or diluent.

In a further aspect, the peptide further comprises the sequence pGlu-His-Pro-Gly-Arg-Arg [SEQ ID NO:4] at the amino terminal portion of the peptide.

In another aspect, there is provided a therapeutically effective amount of the peptide suspended in a pharmaceutically acceptable carrier.

Also included is a kit comprising a CRIF peptide and instructions for using the peptide.

The invention further includes a substantially pure preparation of a CRIF peptide consisting of from three to twenty five contiguous amino acids contained within the amino acid sequence positioned between the fourth and fifth TRH sequence on a prepro-TRH protein.

In one aspect, the peptide consists of a contiguous length of amino acids selected from the group consisting of three, four, five, six, seven, eight, nine, ten, eleven, twelve, thirteen, fourteen, fifteen, sixteen, seventeen, eighteen, nineteen, twenty, twenty one, twenty two, twenty three, twenty four, and twenty five amino acids.

In another aspect, CRIF peptide is human CRIF.

In one embodiment, the peptide consists of from three to twenty five contiguous amino acids of the sequence Leu-Ala-Asp-Pro Lys-Ala-Gln-Arg-Ser-Trp-Glu-Glu-Glu-Glu-Glu-Glu-Glu-Arg-Glu-Glu-Asp-Leu-Met-Pro-Glu [SEQ ID NO:2].

Also included is a therapeutically effective amount of a peptide consisting of from three to twenty five contiguous amino acids contained within the amino acid sequence positioned between the fourth and fifth TRH sequence on a prepro-TRH protein suspended in a pharmaceutically acceptable carrier.

Further included is a kit comprising a CRIF peptide consisting of from three to twenty five contiguous amino acids contained within the amino acid sequence positioned between the fourth and fifth TRH sequence on a prepro-TRH protein, and instructions for using the peptide.

BRIEF DESCRIPTION OF THE DRAWINGS

FIG. 10 shows the amino acid sequence of rat CRIF (SEQ ID NO:1) and the human and mouse homologs of rat CRIF (SEQ ID NO:2 and SEQ ID NO:3, respectively) as well as the nucleotide sequence of rat CRIF (SEQ ID NO:7) and the human and mouse homologs of rat CRIF (SEQ ID NO:8 and SEQ ID NO:9, respectively).

FIG. 17, comprising parts A, B and C, is a series of graphs depicting the anxiolytic properties of CRIF when administered to a rat in vivo. Rats were tested using a light/dark box. Five minutes prior to testing, the animals were injected icv with CRIF or the vehicle. At the beginning of testing, each animal was placed in the center of the light compartment. Behavior was subsequently videotaped for 15 minutes. The behaviors exhibited by the rats were scored by a trained observer who was unaware of the treatment status of each rat. The measures scored were (A) initial latency to enter the dark compartment; (B) number of compartment entries; and (C) total time spent in each compartment.

DETAILED DESCRIPTION

Figure 1:
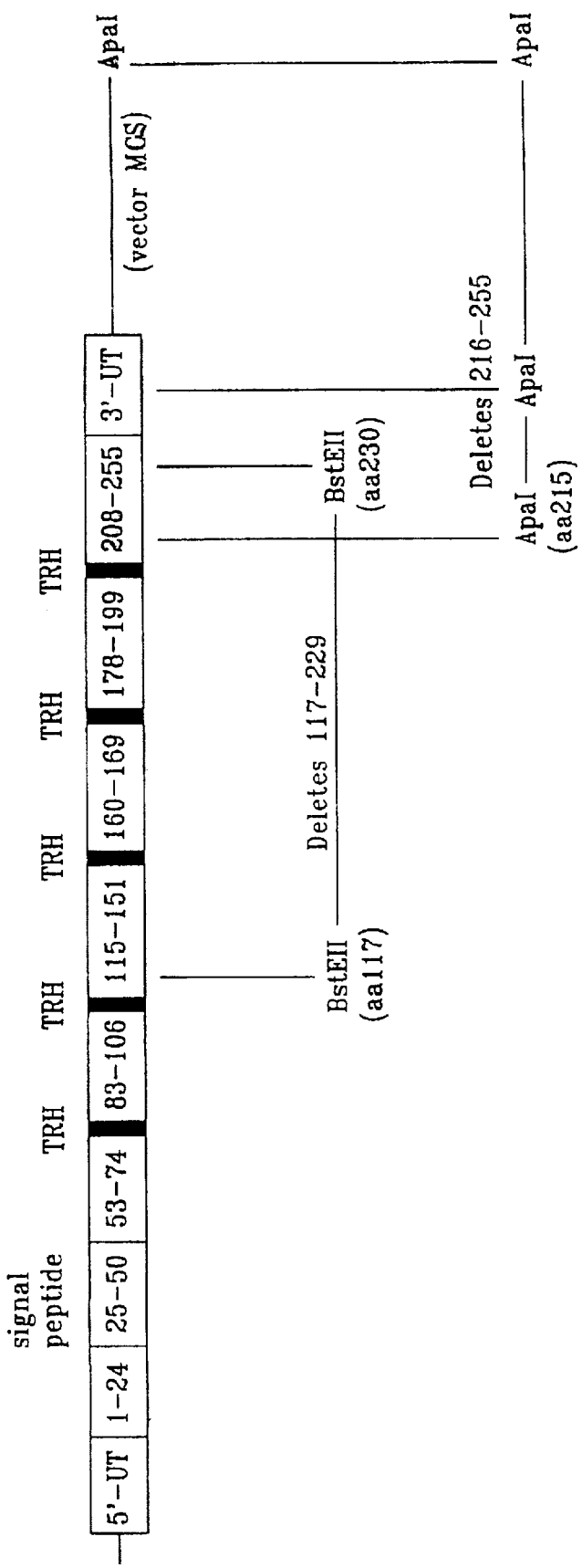
FIG. 1 is a map of the Rat prepro-TRH protein. Groups of amino acids are numbered beginning at the N-terminus of the molecule and the blackened areas indicate the location of each of the five mature TRH tripeptide molecules. The relative positions of the deletions forming plasmids ΔstEII and ΔApaI span the indicated BstEII and ApaI restriction sites.

The present invention relates to a peptide capable of inhibiting both basal and CRF stimulated production of ACTH in cells, which peptide is identified as corticotropin release inhibiting factor (CRIF) and which comprises a portion of the prepro-TRH molecule. The fact that CRIF and TRH are contained within the same precursor suggests an additional and potentially synchronized level of hypothalamic control of ACTH and thyroid stimulating hormone (TSH). TRH and CRIF have opposing regulatory actions on TSH and ACTH levels, respectively. Thus, when prepro-TRH containing neurons secrete high levels of TRH and consequently high levels of CRIF, the level of TSH in the plasma will rise while the level of ACTH will fall. Conversely, when low levels of TRH and CRIF are synthesized, the level of TSH in plasma is diminished, while the level of ACTH is increased. The former situation is known to occur in hypothyroid states when hypothalamic prepro-TRH levels are increased and the latter situation is known to occur in hyperthyroid states when hypothalamic prepro-TRH levels are decreased.

CRIF is useful for treatment of a variety of disorders in mammals, especially humans, wherein the disorders are behavioral in nature. Such disorders include, but are not limited to, Cushing's disease, anxiety disorders, anorexia nervosa, depression, obesity, and withdrawal from alcohol or drug dependence, chronic stress-related syndromes, autoimunne disease, chronic fatigue syndrome, premenstrual syndrome, and symptoms including those exacerbated by stress-induced immunosuppression, such as viral infections. Anxiety disorders include, but are not limited to, generalized anxiety disorder, panic disorder, obsessive-compulsive disorder and post-traumatic stress disorder. CRIF may be used in some cancers (those where an enhanced autoimmune response reduces the severity of the disease), and may increase the efficacy of immunity to vaccines.

As the data provided herein establish, CRIF has a marked effect on the inflammatory immune response, on prolactin secretion, on stress and on behavior. CRIF is thus useful for treatment of a variety of disorders as disclosed herein.

The articles "a" and "an" are used herein to refer to one or to more than one (i.e. to at least one) of the grammatical object of the article. By way of example, "an element" means one element or more than one element.

To generate CRIF for use in treating such disorders, CRIF may be produced synthetically using ordinary synthetic peptide techniques available in the art, or CRIF may be produced in cells comprising DNA encoding CRIF. In the latter instance, it is preferable that the cell be either transiently or stably transfected with DNA encoding CRIF, which DNA is placed under the control of a promoter capable of driving high levels of CRIF transcription in that cell. To generate such a cell, a vector is first generated comprising CRIF DNA positioned downstream from a suitable promoter sequence. The promoter sequence to be used is dependent upon the cell into which the DNA is to be transfected. A plethora of promoter sequences are available commercially which may be used to drive gene expression in a variety of eukaryotic and prokaryotic cells. Thus, the choice of promoter sequence to be used will be apparent to the skilled artisan desiring to transfect a particular cell type with DNA encoding CRIF. Preferably, the promoter sequence is a mammalian promoter sequence, and more preferably, the promoter sequence is derived from human cytomegalovirus. The promoter sequence is considered to be operably linked to the nucleic acid whose expression is desired.

As used herein, the term "promoter/regulatory sequence" means a nucleic acid sequence which is required for expression of a gene product operably linked to the promoter/regulator sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

An "inducible" promoter is a nucleotide sequence which, when operably linked with a polynucleotide which encodes or specifies a gene product, causes the gene product to be produced in a living cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a living cell substantially only if the cell is a cell of the tissue type corresponding to the promoter.

By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region.

The vector of the invention preferably comprises the promoter sequence described above, and also comprises suitable additional DNA sequences which may enhance transcription of DNA encoding CRIF, which may render MnRNA encoding CRIF more stable, and which may even enhance translation of mRNA encoding CRIF. The vector of the invention may comprise a sequence comprising CRIF, or may comprise modifications of that sequence, which modifications specify a CRIF having enhanced properties when compared with wild type or native CRIF. Modification of DNA using recombinant DNA technology is common in the art and is described for example, in Sambrook et al. (1989, Molecular Cloning: A Laboratory Manual, Cold Spring Harbor, N.Y.).

The vector of the invention may comprise any mammalian CRIF DNA sequence. Preferably, the vector of the invention comprises rat, human or mouse CRIF DNA. More preferably, the vector of the invention comprises human CRIF DNA. Preferably, the vector of the invention is pcDNA3(4.5 Kb)-hTRH, or the vector of the invention is pCMV-TRH.

Even more preferably, the vector comprises a minigene having a promoter/regulatory sequence capable of driving CRIF expression, a 5' leader sequence comprising a prepro-TRH leader sequence, a CRIF coding region and translational stop codons, and a 3' sequence being a preproTRH 3' sequence.

Most preferably, when rat CRIF is used, the vector comprises a minigene having a total of 227 base pairs having an 18 base pair multiple cloning restriction enzyme site positioned 5' to a 50 base pair 5' region of a preproTRH gene (wherein the first base pair is at position+1 of the preproTRH sequence), which is positioned 5' to 24 base pairs of pre-proTRH signal sequence, which is positioned 5' to 66 base pairs of CRIF coding sequence, which is positioned 5' to 9 base pairs of a translational stop codon, which is positioned 5' to an 18 base pair multiple cloning restriction enzyme sequence.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses that incorporate the recombinant polynucleotide.

In addition to substantially full length peptides, the present invention provides for biologically active fragments of CRIF.

A CRIF peptide is "biologically active" if it down-regulates both basal and CRF stimulated ACTH secretion in the assays described herein.

As is disclosed herein, peptides having CRIF activity are those which comprise at least three contiguous amino acids contained within the amino acid sequence positioned between the fourth and fifth thyrotropin releasing hormone sequence on a prepro-thyrotropin releasing hormone protein. Full-length CRIF is designated herein as prepro-TRH 178–199, which identifies CRIF as being amino acid numbers 178–199 on the prepro-TRH molecule. However, the invention should in now way be construed as being limited to full-length CRIF. Rather, as the data presented herein establish, peptides which have fewer amino acids than full length CRIF, have CRIF biological activity, as that term is defined herein. For example, peptides having as few as four amino acids and peptides having at least nine amino acids positioned within the prepro-TRH 178–199 molecule have CRIF biological activity according to the results of experiments presented herein.

Full length rodent CRIF peptide comprises twenty two contiguous amino acids in length, wherein CRIF is located between the fourth and fifth TRH in the prepro-TRH molecule. Thus, full length rodent CRIF is also known as prepro-TRH-178–199. Full length human CRIF comprises twenty six contiguous amino acids in length, wherein CRIF is located between the fourth and fifth TRH in the human prepro-TRH molecule.

The invention should be construed to include any and all CRIF peptides comprising amino acid lengths which range from at least three contiguous amino acids to as much as twenty one amino acids in length, being positioned within the prepro-TRH 178–199 molecule. The CRIF peptide of the invention may therefore comprise at least three contiguous amino acids in length, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, up to twenty one contiguous amino acids in length, wherein the peptide is positioned within the prepro-TRH 178–199 molecule.

Preferably, the CRIF peptide of the invention comprises either four or nine amino acids in length. Preferred rodent CRIF sequences include from three to twenty one contiguous amino acid sequences of the SEQ ID NO:1, i.e., Phe-Ile-Asp-Pro-Glu-Leu-Gln-Arg-Ser-Trp-Glu-Glu-Lys-Glu-Gly-Glu-Gly-Val-Leu-Met-Pro-Glu, and SEQ ID NO:3, i.e., Phe-Ile-Asp-Pro-Glu-Leu-Gln-Arg-Ser-Trp-Glu-Glu-Thr-Glu-Gly-Glu-Glu-Gly-Gly-Leu-Met-Pro-Glu, and also all of SEQ ID NO:5, i.e., Glu-Gly-Glu-Gly-Val-Leu-Met-Pro-Glu, and SEQ ID NO:6, i.e., Leu-Met-Pro-Glu, and any derivatives and analogs thereof which retain the biological activity of CRIF as defined herein.

Most preferably, the CRIF peptide of the invention is from three to twenty one contiguous amino acids positioned within the prepro-TRH 178–199 molecule.

With respect to human CRIF, full length human CRIF comprises twenty six contiguous amino acids in length, wherein CRIF is located between the fourth and fifth TRH in the human prepro-TRH molecule. The invention should therefore be construed to include any and all human or other higher mammalian CRIF peptides comprising amino acid lengths which range from at least three contiguous amino acids to as much as twenty five amino acids in length, being positioned within the prepro-TRH 178–199 molecule. The CRIF peptide of the invention may therefore comprise at least three contiguous amino acids in length, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, at least twenty one, at least twenty two, at least twenty three, at least twenty four, and up to twenty five contiguous amino acids in length, wherein the peptide is positioned within the prepro-TRH 178–199 molecule.

A preferred human CRIF is a peptide having from three to twenty five contiguous amino acids of the SEQ ID NO:2, i.e., Leu-Ala-Asp-Pro Lys-Ala-Gln-Arg-Ser-Trp-Glu-Glu-Glu-Glu-Glu-Glu-Glu-Glu-Arg-Glu-Glu-Asp-Leu-Met-Pro-Glu.

The present invention also provides for analogs of peptides having CRIF activity. Analogs can differ from naturally occurring proteins or peptides by conservative amino acid sequence differences or by modifications which do not affect sequence, or by both.

For example, conservative amino acid changes may be made, which although they alter the primary sequence of the protein or peptide, do not normally alter its function. Conservative amino acid substitutions typically include substitutions within the following groups:

glycine, alanine;

valine, isoleucine, leucine;

aspartic acid, glutamic acid;

asparagine, glutamine;

serine, threonine;

lysine, arginine; and phenylalanine, tyrosine.

Other modifications, which do not normally alter the primary sequence but which may be useful, include in vivo or in vitro chemical derivatization of peptides, e.g., amidation, acetylation, or carboxylation, and modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are peptides which have phosphorylated amino acid residues, e.g., phosphotyrosine, phosphoserine, or phosphothreonine.

Also included are peptides which have been modified using ordinary molecular biological techniques so as to improve their resistance to proteolytic degradation or to optimize solubility properties or to render them more suitable as a therapeutic agent. Analogs of such peptides include those containing residues other than naturally occurring L-amino acids, e.g., D-amino acids or non-naturally occurring synthetic amino acids. The peptides of the invention are not limited to products of any of the specific exemplary processes listed herein.

It will thus be appreciated that the peptides may incorporate amino acid residues which are modified without affecting activity. For example, the termini may be derivatized to include blocking groups, i.e. chemical substituents suitable to protect and/or stabilize the N- and C-termini from "undesirable degradation", a term meant to encompass any type of enzymatic, chemical or biochemical breakdown of the compound at its termini which is likely to affect the function of the compound as an anti-inflammatory agent, i.e. sequential degradation of the compound at a terminal end thereof.

Blocking groups include protecting groups conventionally used in the art of peptide chemistry which will not adversely affect the in vivo activities of the peptide. For example, suitable N-terminal blocking groups can be introduced by alkylation or acylation of the N-terminus. Examples of suitable N-terminal blocking groups include $C_1$–$C_5$ branched or unbranched alkyl groups, acyl groups such as formyl and acetyl groups, as well as substituted forms thereof, such as the acetamidomethyl (Acm) group. Desamino analogs of amino acids are also useful N-terminal blocking groups, and can either be coupled to the N-terminus of the peptide or used in place of the N-terminal reside. Suitable C-terminal blocking gruops, in which the carboxyl group of the C-terminus is either incorporated or not, include esters, ketones or amides. Ester or ketone-forming alkyl groups, particularly lower alkyl groups such as methyl, ethyl and propyl, and amide-forming amino groups such as primary amines (—$NH_2$), and mono- and di-alkylamino groups such as methylamino, ethylamino, dimethylamino, diethylamino, methylethylamino and the like are examples of C-terminal blocking groups. Descarboxylated amino acide analogues such as agmatine are also useful C-terminal blocking groups and can be either coupled to the peptide's C-terminal residue or used in place of it. Further, it will be appreciated that the free amino and carboxyl groups at the termini can be removed altogether from the peptide to yield desamino and descarboxylated forms thereof without affect on peptide activity.

Other modifications can also be incorporated without adversely affecting anti-inflammatory activity and these include, but are not limited to, substitution of one or more of the amino acids in the natural L-isomeric form with amino acids in the D-isomeric form. Thus, the peptide may include one or more D-amino acide resides, or may comprise amino acids which are all in the D-form. Retro-inverso forms of peptides in accordance with the present invention are also contemplated, for example, inverted peptides in which all amino acids are substituted with D-amino acid forms.

Acid addition salts of the present invention are also contemplated as functional equivalents. Thus, a peptide in accordance with the present invention treated with an inorganic acid such as hydrochloric, hydrobromic, sulfuric, nitice, phosphoric, and the like, or an organic acid such as an acetic, propionic, glycolic, pyruvic, oxalic, malic, malonic, succinic, maleic, fumaric, tataric, citric, benzoic, cinnamie, mandelic, methanesulfonic, ethanesulfonic, p-toluenesulfonic, salicyclic and the like, to provide a water soluble salt of the peptide is suitable for use in therapeutic settings.

As used herein, amino acids are represented by the full name thereof, by the three letter code corresponding thereto, or by the one-letter code corresponding thereto, as indicated in the following table:

| Full Name | Three-Letter Code | One-Letter Code |
| --- | --- | --- |
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer.

The term "protein" typically refers to large polypeptides.

The term "peptide" typically refers to short polypeptides.

Conventional notation is used herein to portray polypeptide sequences: the left-hand end of a polypeptide sequence is the amino-terminus; the right-hand end of a polypeptide sequence is the carboxyl-terminus.

Novel biological antagonists and agonists of CRIF are also contemplated in the invention. A compound is a biological inhibitor of CRIF if it inhibits the synthesis or function of the naturally occurring CRIF peptide in the assays described herein. A compound is a biological activator of CRIF if it activates the synthesis or function of CRIF in the assays described herein. Naturally occurring compounds are known, such as thyroid hormones and glucocorticoids. However, the invention contemplates other compounds which may now be identified in view of the discovery of CRIF.

As used herein, the term "substantially pure" describes a compound, e.g., a peptide which has been separated from components which naturally accompany it. Typically, a compound is substantially pure when at least 10%, more preferably at least 20%, more preferably at least 50%, more preferably at least 60%, more preferably at least 75%, more preferably at least 90%, and most preferably at least 99% of the total material (by volume, by wet or dry weight, or by mole percent or mole fraction) in a sample is the compound of interest. Purity can be measured by any appropriate method, e.g., in the case of peptides by column chromatography, gel electrophoresis or HPLC analysis. A compound, e.g., a peptide is also substantially purified when it is essentially free of naturally associated components or when it is separated from the native contaminants which accompany it in its natural state.

An "isolated nucleic acid", as used herein, refers to a nucleic acid sequence, segment, or fragment which has been purified from the sequences which flank it in a naturally occurring state, e.g., a DNA fragment which has been removed from the sequences which are normally adjacent to the fragment e.g., the sequences adjacent to the fragment in a genome in which it naturally occurs. The term also applies to nucleic acids which have been substantially purified from other components which naturally accompany the nucleic acid, e.g., RNA or DNA or proteins which naturally accompany it in the cell.

A "recombinant cell", as used herein, refers to a cell having within it one or more copies of an isolated nucleic acid, which nucleic acid is added to the cell by recombinant DNA techniques.

"Complementary" as used herein, refers to the subunit sequence complementarity between two nucleic acid molecules, e.g., two DNA molecules or two RNA molecules. When a subunit position in both of the two molecules is occupied by a complementary monomeric subunit, e.g., if one position in each of two DNA molecules is occupied by adenine and the other is occupied by a thymine, then they are complementary at that position. Similarly, if one position in each of two DNA molecules is occupied by guanine and the other is occupied by a cytosine, then they too are complementary at that position. The degree of complementarity between two sequences is a direct function of the number of positions occupied by complementary bases, e.g., if half (e.g., five positions in a polymer ten subunits in length) of the positions in two compound sequences contain complementary bases then the two sequences share 50% complementarity, if 90% of the positions, e.g., 9 of 10, contain bases complementary to each other, the two sequences share 90% complementarity. By way of example, the DNA sequences 5'ATTGCC3' and 3'GGCGCC5' share 50% complementarity.

It should be emphasized herein that the invention also includes an isolated nucleic acid molecule encoding CRIF, or any biologically active fragment thereof. The isolated nucleic acid of the invention may be one which encodes a biologically active CRIF molecule having at least three contiguous amino acids in length, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, up to twenty one contiguous amino acids in length, wherein the peptide is positioned within the prepro-TRH 178–199 molecule. Preferably, the isolated nucleic acid encoding CRIF encodes a CRIF molecule having either four or nine amino acids in length.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom.

Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

CRIF or agonists and antagonists thereof, can be used to treat a variety of disorders in humans. CRIF may be used to modulate hypothalamic pituitary adrenal (HPA) activity in the brain, the pituitary and/or the immune system. Increases in HPA activity are defined by increased hypothalamic CRF and/or increased pituitary ACTH and/or increased adrenocortical glucocorticoid production. Illness associated with hypercortisolemia such as Cushing's disease, anxiety disorders, anorexia nervosa, depression, obesity, and withdrawal from alcohol or drug dependence, may be treated with CRIF in order to reduce ACTH levels. Regarding depression, hypercortisolemia is believed to contribute to the etiology of depression and therefore, CRIF may be useful for treatment of depression. CRIF may even be used to control appetite.

CRIF may also be used to reduce ACTH and cortisol levels for treatment of chronic stress-related syndromes and symptoms including those exacerbated by stress-induced immunosuppression, such as viral infections. CRIF may be used in some cancers (those where an enhanced autoimmune response reduces the severity of the disease), and may increase the efficacy of immunity to vaccines. Anti-CRIF antibodies or other CRIF antagonists may be used to counteract the effects of CRIF during illness and may therefore be useful for treatment of hypocortisolism, isolated ACTH deficiency and premenstrual syndrome. CRIF antibodies or antagonists may also be used to systemically treat illnesses with an inflammatory component, such as colitis, and autoimmune diseases such as arthritis, conditions in which higher levels of endogenous glucocorticoids are advantageous.

Inflammatory diseases which are treatable according to the methods and compositions of the invention include, but are not limited to, diseases which are characterized as having an acute inflammatory immune response component, such as those which are characterized as having irregular or periodic episodes of acute inflammatory immune responses components as well as those which are termed "autoimmune" a designation commonly used in the art. Typically, such autoimmune diseases include systemic autoimmune diseases such as systemic lupus erythematosus, multiple sclerosis and rheumatoid arthritis. Examples of these and other inflammatory diseases may be found in any common immunology textbook, for example, in Stites et al., 1984, Basic and Clinical Immunology, $5^{th}$ Edition, Lange.

CRIF itself can be used locally to ameliorate inflammation as it is known that CRF is released locally at sites of inflammation wherein it appears to act as an autocrine or paracrine inflammatory cytokine (Karalis et al., 1991, Science 254:421). Since local CRF induces synthesis of POMC in lymphocytes, the actual mediators of these inflammatory responses may be POMC-related peptides. Thus, inhibition of the local production of POMC peptides by locally administered CRIF should ameliorate inflammatory autoimmune disease.

The current treatment of choice in ACTH disorders involves the use of glucocorticoids. Since most cells contain glucocorticoid receptors, this type of treatment induces significant side effects. In contrast, treatment using CRIF is expected to be associated with minimal overall side effects since CRIF acts specifically upon ACTH synthesizing and ACTH secreting cells. In fact, as the data provided herein establish, rats treated in vivo with CRIF exhibit no discernible deleterious side effects associated with CRIF administration.

Protocols for treatment of mammals with a CRIF disorder involving administration of an agonist or antagonist, or of CRIF itself, will be apparent to those skilled in the art and will vary depending upon the type of disease, and the type and age of the mammal. Treatment regimes which are contemplated include a single dose or dosage which is administered hourly, daily, weekly or monthly, or yearly. Dosages may vary from 1 μg to 1000 mg/kg of body weight of the agonist or antagonist, or of CRIF and will be in a form suitable for delivery of the compound. The route of administration may also vary depending upon the disorder to be treated.

The invention contemplates administration of CRIF to humans for the dual purpose of either treating or diagnosing a human having a CRIF disorder. The protocol which is described below for administration of CRIF to a human is provided as an example of how to administer CRIF to a human. This protocol should not be construed as being the only protocol which can be used, but rather, should be construed merely as an example of the same. Other protocols will become apparent to those skilled in the art when in possession of the instant invention. Essentially, for administration to humans, CRIF is dissolved in about 1 ml of saline and doses of 1 μg, 10 μg and 100 μg per kg of body weight are administered intravenously at 48 hour intervals. Cardiovascular and neuroendocrine function are monitored throughout the administration period.

The agonist, antagonist or CRIF is prepared for administration by being suspended or dissolved in a pharmaceutically acceptable carrier such as saline, salts solution or other formulations apparent to those skilled in such administration. The compositions of the invention may be administered to a mammal in one of the traditional modes (e.g., orally, parenterally, transdermally or transmucosally), in a sustained release formulation using a biodegradable biocompatible polymer, or by on-site delivery using micelles, gels and liposomes, or rectally (e.g., by suppository or enema) or nasally (e.g., by nasal spray). The appropriate pharmaceutically acceptable carrier will be evident to those skilled in the art and will depend in large part upon the route of administration.

Agonists or antagonists of CRIF include, but are not limited to, antibody to CRIF, a nucleic acid sequence complementary to DNA encoding CRIF, and even peptidometics. Peptidometics having CRIF-like activity include compounds which have a sufficient CRIF-like activity such that their effects on the disease being treated are beneficial to the individual being treated, which beneficial effects are similar to that of CRIF. Peptidometics may also have additional advantages over CRIF in that they may be designed such that they are capable of accessing targets which are normally relatively inaccessible to CRIF. For example, as described herein, CRIF, when administered directly into the brain of an animal, has a beneficial effect on the behavior of that animal. However, since CRIF is a peptide, it is expected that the amount of unmodified CRIF which eventually reaches the brain following intravenous administration of CRIF to an animal will be minimal. The peripheral administration to the animal of a peptidometic having CRIF activity, which peptidometic is capable of crossing the blood-brain barrier, circumvents this problem.

"CRIF-like activity" as used here denotes an activity which is so similar to that of CRIF, i.e., which functions by the same mechanism as CRIF, so as to be virtually indistinguishable from CRIF. However, this term as used herein, should also be construed to encompass compounds which may operate by the same mechanism as CRIF, but which may have a higher specific activity than CRIF.

"Peripheral administration" as used herein, denotes administration of a compound to an animal by any route other than direct administration to the brain. Thus, peripheral administration includes, but is not limited to, oral, nasopharyngeal, intraperitoneal, intramuscular and intravenous administration of any of the compounds of the invention.

Similarly, peptidometics having CRIF-antagonist-like or CRIF-agonist-like activity may also be designed and used according to the methods of the present invention. Such CRIF-antagonist and agonist peptidometics may be administered to the animal by any peripheral route in order that they eventually reach the target area in the animal wherein they exert their effects. Additional information describing administration of peptidometics is provided in PCT/US93/01201 and U.S. Pat. No. 5,334,702, which are hereby incorporated herein by reference. Any of the techniques described in either of these two references may be employed in the present invention for the administration of peptidometics.

Peptidometics may be generated using techniques described in PCT/US93/01201 and in U.S. Pat. No. 5,334,702. Generation of anti-CRIF antibodies is described below. Nucleic acid sequence complementary to CRIF may be generated using the sequence of CRIF provided herein. Administration of antisense oligonucleotides to mammals is now common in the art and may be accomplished by using any of the administration techniques described herein.

Preferably, the CRIF of the invention is administered at a dose of 1 μg to 100 mg/kg body weight and the CRIF agonist or antagonist is administered at a dose of 1 μg to 100 mg/kg of body weight.

Compounds having CRIF, CRIF antagonist or agonist activity or which have CRIF-like activity also include compounds which are formulated so as to target specific types of cells. For example, it is now known in the art to encapsulate or otherwise formulate compounds such that they are directed to specific receptors on cells. Such formulations include antibody-tagging formulations, receptor-ligand binding formulations and the like.

The invention also includes a method of treating an inflammatory disease in a human by increasing the level of endogenous glucocorticoids in the human. The method comprises administering a CRIF antagonist to the human. Preferably, the CRIF antagonist is an anti-CRIF antibody. One or more CRIF antagonists may be administered to the human either alone, or in combination with the thyroid hormones, $T_3$ or $T_4$. The thyroid hormones are administered by any convenient route, including orally, parenterally, transdermally, transmucosally, or rectally or nasally. The amount of CRIF antagonist to be administered and the amount of thyroid hormone to be administered if so desired, will be apparent to one of skill in the art of inflammatory disease. Preferably, the thyroid hormone is administered as described herein for either $T_3$ or $T_4$, and the CRIF antagonist is administered at a dose of 1 Ig to 100 mg/kg of body weight daily.

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and $F(ab)_2$, as well as single chain antibodies and humanized antibodies (Harlow et al., 1999, Using Antibodies: A Laboratory Manual, Cold Spring Harbor Laboratory Press, N.Y.; Harlow et al., 1989, Antibodies: A Laboratory Manual, Cold Spring Harbor, N.Y.; Houston et al., 1988, Proc. Natl. Acad. Sci. USA 85:5879–5883; Bird et al., 1988, Science 242:423–426).

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

It is also apparent from the data described herein that thyroid hormones may be administered to the animal without the added administration of a CRIF antagonist, for the purpose of modulating inflammatory diseases. In view of the effect of the thyroid hormones $T_3$ and $T_4$ on CRIF as demonstrated herein, thyroid hormones themselves are useful as therapeutic compounds for treatment of CRIF-related disorders. In particular, in view of the data provided herein, the thyroid hormones, $T_3$ or $T_4$, may be administered to the animal to reduce or abate inflammatory disease.

$T_3$ or $T_4$ may be administered to the animal in an unmodified form, or in a form designed to increase the stability and/or the specific activity of $T_3$ or $T_4$ in the animal. Such modifications include those described herein with respect to CRIF. In addition to modifications of $T_3$ or $T_4$, compounds having $T_3$ or $T_4$ activity may also be generated using the technology described herein.

$T_3$ or $T_4$, modified $T_3$ or $T_4$, or a compound having $T_3$- or $T_4$-like activity, may be formulated in any of the formulations described herein with respect to CRIF. Typically, $T_3$, modified $T_3$, or a compound having $T_3$-like activity, is administered to the animal in a dose of about 10 μg to about 150 μg per adult human. Preferably, $T_3$, modified $T_3$, or a compound having $T_3$-like activity, is administered to the animal in a dose of about 15 μg to about 100 μg per adult human, and even more preferably, the dose is in the range of about 25 μg to about 75 μg per adult human.

$T_4$, modified $T_4$, or a compound having $T_4$-like activity, is typically administered to the animal in a dose of about 0.05 mg to about 0.8 mg per adult human. Preferably, $T_4$, modified $T_4$, or a compound having $T_4$-like activity, is administered to the animal in a dose of about 0.075 mg to about 0.6 mg per adult human, and even more preferably, the dose is in the range of about 0.1 mg to about 0.4 mg per adult human.

By "$T_3$-like activity" or by "$T_4$-like activity" as used herein, is meant compounds which have an activity which is so similar to that of either of $T_3$ or $T_4$, respectively, i.e., which functions by the same mechanism as $T_3$ or $T_4$, so as to be virtually indistinguishable from either of $T_3$ or $T_4$, respectively. However, this term as used herein, should also be construed to encompass compounds which may operate by the same mechanism as either of $T_3$ or $T_4$, but which may have a higher specific activity than either of $T_3$ or $T_4$.

Compounds having $T_3$- or $T_4$-like activity also include compounds which are formulated so as to target specific types of cells. For example, it is now known in the art to encapsulate or otherwise formulate compounds such that they are directed to specific receptors on cells. Such formulations include antibody-tagging formulations, receptor-ligand binding formulations and the like.

$T_3$, $T_4$, modified $T_3$ or $T_4$, or compounds having $T_3$- or $T_4$-like activity may be prepared for administration by being suspended or dissolved in a pharmaceutically acceptable carrier such as saline, salts solution or other formulations apparent to those skilled in such administration. The compositions of the invention may be administered to a mammal in one of the traditional modes (e.g., orally, parenterally, transdermally or transmucosally), in a sustained release formulation using a biodegradable biocompatible polymer, or by on-site delivery using micelles, gels and liposomes, or rectally (e.g., by suppository or enema) or nasally (e.g., by nasal spray). The appropriate pharmaceutically acceptable carrier will be evident to those skilled in the art and will depend in large part upon the route of administration.

In addition to treatment of disease using CRIF or agonists or antagonists thereof, anti-CRIF antibody may be used to diagnose CRIF-related diseases in mammals suspected of having such diseases. For example, samples of blood may be obtained from mammals suspected of having a CRIF-related disease or from normal individuals. Antibody is added to each blood sample and the amount of CRIF in the sample bound to the antibody is measured using ordinary antibody measuring techniques such as Enzyme Linked Immunoabsorbant Assay (ELISA) or Radioimmunoassay (RIA). A higher or lower amount of antibody bound to the CRIF in the mammal's blood compared with normal blood is an indication that the mammal has a CRIF-related disease. These types of diagnostic tests are well known in the art and are used for measurement of serum levels of other hormones such as ACTH, cortisol or even TRH.

Anti-CRIF antibodies are easily generated by immunization of an animal with the CRIF peptide identified herein. Protocols for the generation of antibodies (either monoclonal or polyclonal antibodies) to a known peptide are described in Harlow et al. (1988, In: Antibodies, A Laboratory Manual, Cold Spring Harbor, N.Y.), which protocols can be easily followed by the skilled artisan. Polyclonal antibodies to CRIF may be raised in any suitable animal, such as a mouse or a rabbit. Monoclonal anti-CRIF antibodies are generated by immunization of a mouse with CRIF peptide followed by production of hybridoma cells capable of secreting anti-CRIF antibody.

Diagnostic tests for the identification of CRIF-related disease states are not limited to the use of anti-CRIF antibody. Other tests may also be used including nucleic acid based tests such as hybridization and/or polymerase chain reaction (PCR) assays. In this instance, samples of cells or tissue are obtained from blood (lymphocytes, platelets), the pituitary or the placenta or amniotic fluid of normal healthy mammals or mammals suspected of having a CRIF-related disease, which samples are processed for hybridization or PCR assays following ordinary protocols described for example, in Sambrook et al. (1989, Molecular Cloning: A Laboratory Manual, Cold Spring Harbor, N.Y.). Probes and primers which can be used in these assays include nucleic acid sequences comprising CRIF, which sequences are described herein.

An additional diagnostic test may be used which test takes advantage of the ability of CRIF to affect levels of ACTH. In this test, a bolus dose of CRIF (1 μg-1000 mg/kg body weight) is administered to a mammal suspected of having a CRIF disorder. Plasma levels of ACTH and cortisol are then measured in the mammal. In cases where CRIF is underproduced in the mammal, levels of ACTH will be more suppressed compared with those in a normal mammal. In cases where CRIF is overproduced, levels of ACTH will be less suppressed than those in a normal mammal. Thus, this test is a measure of under or over production of CRIF as assessed by the level of ACTH in a mammal. This test may be useful in situations wherein direct measurement of CRIF proves difficult.

There are two general animal models which may be used to test the efficacy of CRIF in some of the diseases described herein. In the first model, hypersecretion of ACTH, generation of ulcers and depressive behavior can be examined. In this model the Wistar-Kyoto (WKY) rat, which exhibits hypersecretion of ACTH and enhanced synthesis of anterior pituitary ACTH, is used. Hypersecretion of ACTH and enhanced synthesis of anterior pituitary ACTH is measured by measuring levels of POMC mRNA, which in this case are increased compared with other rat strains (Redei et al., 1994, Am. J. Physiol. 266:R353–R360). The WKY rat also exhibits increased vulnerability to stress ulcer and spontaneous depressive behavior as measured in different paradigms including the Porsolt swim test, a test used for screening of anti-depressant agents (Pare and Redei, 1993, J. Physiol. 87:229–238).

To test the efficacy of CRIF, WKY rats are pretreated with intravenous injection of CRIF suspended in saline at a concentration of 1–10 $\mu$g/kg of body weight Struggling time and floating time of treated animals is compared with that exhibited by control animals administered saline alone. Increased struggling time and decreased floating time during the length of the test (15 minutes) is expected if CRIF acts as an anti-depressant. To determine the effect of CRIF on acquisition of stress ulcers, animals are treated as described above, exposed to water restraint and the number of ulcers in treated versus untreated rats is measured (Pare and Redei, 1993, J. Physiol. 87:229–238). It is expected that CRIF treated WKY rats will have fewer ulcers than their untreated counterparts.

In the second animal model, the female Lewis rat, which rat exhibits increased susceptibility to autoimmune illness, is used (Sternberg et al., 1989, Proc. Natl. Acad. Sci. USA 86:2374–2378). This increased susceptibility seems to correlate with an inability to mount an appropriate glucocorticoid response to an inflammatory agent. When these animals are either stressed or are treated with glucocorticoids, their autoimmune condition improves suggesting that their low levels of ACTH and glucocorticoids are responsible for their increased vulnerability to autoimmune illness.

To perform this second test, female Lewis rats are pretreated with anti-CRIF antibody and their ability to mount an enhanced ACTH and glucocorticoid response to an inflammatory agent is assessed and compared with that response exhibited by untreated animals.

A frequently used animal inflammatory response model involves induction of arthritis by systemic injection of a streptococcal cell wall (SCW) preparation. In this model, the animals become arthritic following injection of the cell wall preparation. To examine the effect of CRIF in this model, female Lewis rats are implanted with osmotic minipumps that are designed to deliver a continuous intravenous flow of anti-CRIF antibody approximately one week prior to administration of the SCW preparation. Administration of anti-CRIF antibody is expected to increase ACTH levels and consequently glucocorticoid levels, thus rendering Lewis rats less susceptible to arthritis. Sprague-Dawley rats which do not exhibit increased susceptibility to autoimmune illness may be used as a control.

CRIF is also useful for treatment of diseases associated with increased prolactin secretion since, as described herein, CRIF inhibits secretion of prolactin. Prolactin, which plays a major role in milk production in animals, is a large peptide which is produced by the anterior pituitary by lactotrophs, somatotrophs and by cells in the placenta. Somatotrophs also produce growth hormone and in fact, prolactin is a member of the same peptide family as growth hormone peptide. Receptors for human prolactin have been cloned. Such receptors are found in T cells, B cells, cells of the testes and ovaries, and large amounts of prolactin receptors are found in mammary glands. Secretion of prolactin is induced by stress and by suckling. Further, there is evidence that the effect of prolactin on cells occurs via a negative type of regulation. Prolactin is reviewed in DeGroot. 1989, Endocrinology, W. B. Saunders Co.

The ability of CRIF to inhibit prolactin secretion is clinically important. For example, hyperprolactonemia can lead to amenorrhea/galactorrhea and gynecomastia in humans. Further, hyperprolactinemia in human males is associated with a decrease in libido and potency and in some cases hypogonadism. In addition, chronic anovulation in women is attributed to prolactin hypersecretion (Palermo et al., 1994, "Chronic anovulation due to prolactin hypersecretion" Acta Europaca Fertilitatis 25(3): 161–172). All of these symptoms are reversed by reducing prolactin levels (DeGroot. 1989, Endocrinology, W. B. Saunders Co.).

Prolactin also plays a role in immune function, by increasing the immune responsiveness of T cells and other immune cells. For example, some T cells require prolactin for proliferation (Prystowsky et al., 1994, Immunomethods 5(1): 49–55). Further, prolactin is known to play a role in autoimmune diseases such as systemic lupus erythematosus (Walker et al., 1995, "Epidemiology of rheumatoid arthritis" Lupus 4(1): 3–9) and rheumatoid arthritis (Silman, 1994, APMIS 102(10): 721–728).

In addition to the above, prolactin is an important component in breast cancer and other tumors having prolactin receptors. In at least the latter instance, prolactin plays a role in stimulating the growth of cells. Thus, inhibition of prolactin secretion using CRIF provides a means of cells growth inhibition and therefore tumor growth inhibition (Zumoff, 1994, "Hormonal profiles in women with breast cancer", Obstetrics & Gynecology Clinics of North America 21(4): 751–772).

Some of the endocrine consequences of hyperprolactinemia are currently treated with the dopamine receptor agonist bromocriptine mesylate (Parlodel™, Sandoz). According to the present invention, treatment of individuals with CRIF provides yet another therapeutic paradigm for prolactin-associated disorders. Prolactin-associated disorders therefore include, but are not limited to hyperprolactonemia-associated diseases including amenorrhea/galactorrhea and gynecomastia, decreased in libido and potency, hypogonadism, chronic anovulation, immune disorders including autoimmune diseases such as systemic lupus erythematosus and rheumatoid arthritis, and breast cancer and other tumors having prolactin receptors.

CRIF is also useful for treatment of behavioral disorders in animals and humans. As the data provided herein establish, CRIF has marked effects on the behavior of animals administered this peptide. The behavioral responses following icv administration indicate that CRIF has neurobehavioral effects in addition to its regulatory role in anterior pituitary ACTH and prolactin release. The results of the experiments described herein suggest that CRIF possesses arousal and anxiolytic properties. The data further suggest that the observed neuroendocrine and behavioral response in rats administered CRIF may be activated simultaneously by independent mechanisms.

CRIF, or a peptidometic having CRIF-like activity, may be useful for treatment of behavioral symptoms associated with anxiety disorders. Such anxiety disorders include, but are not limited to generalized anxiety disorder, panic disorder, obsessive-compulsive disorder and post-traumatic stress disorder (American Psychiatric Association: Diagnostic and Statistical Manual of Mental Disorders: DSM-IV, Washington, D.C. American Psychiatric Association, 1994).

As used herein, "treating a CRIF-related" means reducing the frequency with which a symptom of the CRIF-related disorder is experienced by a patient.

A "prophylactic" treatment is a treatment administered to a subject who does not exhibit signs of a disease or exhibits only early signs of the disease for the purpose of decreasing the risk of developing pathology associated with the disease.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

By the term "CRIF-related disorder" as used herein is meant any disease or disorder in a mammal which can be alleviated, prevented or otherwise treated by manipulating CRIF in the mammal.

Compounds which are identified using any of the methods described herein may be formulated and administered to a mammal for treatment of a CRIF-related disorder are now described.

The invention encompasses the preparation and use of pharmaceutical compositions comprising a compound useful for treatment of a CRIF-related disorder as an active ingredient. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

As used herein, the term "pharmaceutically acceptable carrier" means a chemical composition with which the active ingredient may be combined and which, following the combination, can be used to administer the active ingredient to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates and mammals including commercially relevant mammals such as cattle, pigs, horses, sheep, cats, and dogs.

Pharmaceutical compositions that are useful in the methods of the invention may be prepared, packaged, or sold in formulations suitable for oral, rectal, vaginal, parenteral, topical, pulmonary, intranasal, buccal, ophthalmic, intrathecal or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Particularly contemplated additional agents include anti-emetics and scavengers such as cyanide and cyanate scavengers.

Controlled- or sustained-release formulations of a pharmaceutical composition of the invention may be made using conventional technology.

A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

As used herein, an "oily" liquid is one which comprises a carbon-containing liquid molecule and which exhibits a less polar character than water.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically-controlled release tablets. Tablets may further comprise a sweetening agent, a flavoring agent, a coloring agent, a preservative, or some combination of these in order to provide a pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Liquid formulations of a pharmaceutical composition of the invention which are suitable for oral administration may be prepared, packaged, and sold either in liquid form or in the form of a dry product intended for reconstitution with water or another suitable vehicle prior to use.

Liquid suspensions may be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g. polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may fritter comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non-irritating pharmaceutically acceptable excipient which is solid at ordinary room temperature (i.e. about 20° C.) and which is liquid at the rectal temperature of the subject (i.e. about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants and preservatives.

Retention enema preparations or solutions for rectal or colonic irrigation may be made by combining the active ingredient with a pharmaceutically acceptable liquid carrier. As is well known in the art, enema preparations may be administered using, and may be packaged within, a delivery device adapted to the rectal anatomy of the subject. Enema preparations may further comprise various additional ingredients including, but not limited to, antioxidants and preservatives.

A pharmaceutical composition of the invention may be prepared, packaged, or sold in a formulation suitable for vaginal administration. Such a composition may be in the form of, for example, a suppository, an impregnated or coated vaginally-insertable material such as a tampon, a douche preparation, or gel or cream or a solution for vaginal irrigation.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e. such as with a physiologically degradable material), and methods of absorbing an aqueous or oily solution or suspension into an absorbent material, with or without subsequent drying.

Douche preparations or solutions for vaginal irrigation may be made by combining the active ingredient with a pharmaceutically acceptable liquid carrier. As is well known in the art, douche preparations may be administered using, and may be packaged within, a delivery device adapted to the vaginal anatomy of the subject. Douche preparations may further comprise various additional ingredients including, but not limited to, antioxidants, antibiotics, antifungal agents, and preservatives.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Formulations suitable for topical administration include, but are not limited to, liquid or semi-liquid preparations such as liniments, lotions, oil-in-water or water-in-oil emulsions such as creams, ointments or pastes, and solutions or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65 ° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the invention.

Another formulation suitable for intranasal administration is a coarse powder comprising the active ingredient and having an average particle from about 0.2 to 500 micrometers. Such a formulation is administered in the manner in which snuff is taken i.e. by rapid inhalation through the nasal passage from a container of the powder held close to the nares.

Formulations suitable for nasal administration may, for example, comprise from about as little as 0.1% (w/w) and as much as 100% (w/w) of the active ingredient, and may further comprise one or more of the additional ingredients described herein.

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

A pharmaceutical composition of the invention may be prepared, packaged, or sold in a formulation suitable for ophthalmic administration. Such formulations may, for example, be in the form of eye drops including, for example, a 0.1–1.0% (w/w) solution or suspension of the active ingredient in an aqueous or oily liquid carrier. Such drops may further comprise buffering agents, salts, or one or more other of the additional ingredients described herein. Other ophthalmalmically-administrable formulations which are useful include those which comprise the active ingredient in microcrystalline form or in a liposomal preparation.

As used herein, "additional ingredients" include, but are not limited to, one or more of the following: excipients; surface active agents; dispersing agents; inert diluents; granulating and disintegrating agents; binding agents; lubricating agents;

sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants;

antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., (1985, Remington's Pharmaceutical Sciences, Mack Publishing Co., Easton, Pa.), which is incorporated herein by reference.

Typically dosages of the compound of the invention which may be administered to an animal, preferably a human, range in amount from 1 μg to about 100 g per kilogram of body weight of the animal. While the precise dosage administered will vary depending upon any number of factors, including but not limited to, the type of animal and type of disease state being treated, the age of the animal and the route of administration. Preferably, the dosage of the compound will vary from about 1 mg to about 10 g per kilogram of body weight of the animal. More preferably, the dosage will vary from about 10 mg to about 1 g per kilogram of body weight of the animal.

The compound may be administered to an animal as frequently as several times daily, or it may be administered less frequently, such as once a day, once a week, once every two weeks, once a month, or even lees frequently, such as once every several months or even once a year or less. The frequency of the dose will be readily apparent to the skilled artisan and will depend upon any number of factors, such as, but not limited to, the type and severity of the disease being treated, the type and age of the animal, etc.

The invention also includes a kit comprising the composition of the invention and an instructional material which describes adventitially administering the composition to a cell or a tissue of a mammal. In another embodiment, this kit comprises a (preferably sterile) solvent suitable for dissolving or suspending the composition of the invention prior to administering the compound to the mammal.

As used herein, an "instructional material" includes a publication, a recording, a diagram, or any other medium of expression which can be used to communicate the usefulness of the peptide of the invention in the kit for effecting alleviation of the various diseases or disorders recited herein. Optionally, or alternately, the instructional material may describe one or more methods of alleviation the diseases or disorders in a cell or a tissue of a mammal. The instructional material of the kit of the invention may, for example, be affixed to a container which contains the peptide of the invention or be shipped together with a container which contains the peptide. Alternatively, the instructional material may be shipped separately from the container with the intention that the instructional material and the compound be used cooperatively by the recipient.

The invention is now described with reference to the following examples. These examples are provided for the purpose of illustration only and the invention should in no way be construed as being limited to these examples but rather should be construed to encompass any and all variations which become evident as a result of the teaching provided herein.

EXAMPLES

It has now been discovered that CRIF is comprised of a peptide which is a component of the hypothalamic prepro-thyrotropin-releasing hormone (prepro-TRH) in that it is present within one of the TRH intervening sequences. This discovery was based upon the observation that prepro-TRH, but not the mature TRH tripeptide, is capable of inhibiting both basal and stress- or CRF-induced ACTH synthesis and secretion. The only pathophysiologically meaningful condition in which both basal and stress-induced ACTH levels are suppressed is in the hypothyroid state. In this state, elevated levels of hypothalamic prepro-TRH are observed, yet mature TRH does affect ACTH secretion (Segerson et al., Science 238:78, 1987). Rat pro-TRH comprises 255 amino acids and contains 5 copies of the TRH tripeptide plus seven intervening sequences (Lechan et al., 1986, Science, 231:159–161). In the experiments described herein, a cDNA encoding prepro-TRH was transfected into AtT-20 cells, a mouse pituitary tumor cell line which expresses and processes POMC, the precursor of ACTH, and which cell line processes prepro-TRH (Sevarino et al., 1989, J. Biol. Chem. 264:215229–215235; Nillni et al., 1993, Endocrinology 132:1260–1270). Transient transfection with prepro-TRH results in inhibition, in a dose response manner, of both synthesis and secretion of ACTH under unstimulated and CRF-stimulated conditions.

Cell cultures

AtT-20 cells (Sabol, 1980, Arch. Biochem. Biophys. 203:37–48) were maintained and subcultured in DMEM supplemented with 10% fetal calf serum plus antibiotics in a humidified 10% $CO_2$ atmosphere. In the experiments described herein, the cells were incubated in steroid-free (charcoal-stripped) fetal calf serum (FCS).

Extraction and Chromatography of CRIF

Hypothalamic extracts from adult male Wistar and WKY rats were prepared as described by Redei et al. (In: Neuropeptides and Stress, Eds. Tache et al., Hans Selye Symposia on Neuroendocrinology and Stress, 1989, Springer-Verlag, N.Y.). Briefly, 10 hypothalami each were suspended in water containing 0.1% ascorbic acid and 200 KIU/ml aprotinin (Sigma). The suspension was centrifuged at 10,000×g at 4° C. for 30 min. Supernatants were filtered through a Sephadex G-50 (fine) column at a flow rate of 0.25 ml/min using 50% acetic acid as eluent. Two minute fractions were collected and evaporated to dryness in a Speed-Vac concentrator (Savant System Inc.,). Fractions were bioassayed using AtT-20 cells in the CRIF assay. Those fractions exhibiting CRIF activity were collected and stored until further experimentation.

Plasmids

The expression vector pCMV-TRH comprises cDNA encoding rat TRH under the control of the human cytomegalovirus (HCMV) immediate early promoter (Lee et al., 1988, J. Biol. Chem. 263:16604–16609). To generate this vector, a 1,322 bp fragment comprising sequences encoding TRH was excised from the plasmid pSP64, by digestion with HindIII and EcoRI. This fragment was then inserted into pcDNA-3 (Invitrogen, San Diego, Calif.) to generate pCMV-TRH comprising the HCMV immediate early promoter, the bovine growth hormone polyadenylation signal and cDNA encoding TRH inserted therebetween. This plasmid also contains sequences encoding resistance to neomycin and can therefore be used to select stably transfected cells. The structure of the rat prepro-TRH molecule is presented in FIG. 1.

Referring to FIG. 1, two deletions were made in the expression vector pCMV-TRH. The first deletion, ΔBstEII, contains a deletion between nucleotides 506 and 787 in TRH cDNA. This results in deletion of amino acids 117 to 229 of prepro-TRH. To generate ΔBstEII, pCMV-TRH was digested with BstEII, and a 6.4 kb fragment was isolated therefrom. The 5' sticky ends were filled in with Klenow to create blunt ends, and the 6.4 kb fragment was then religated to form ΔBstEII. This religation results in restoration of the original wild type reading frame. The second deletion, ΔApaI, contains a deletion from nucleotides 746 in the prepro-TRH molecule to the ApaI site in the pcDNA-3 vector immediately downstream from the prepro-TRH cDNA insert (i.e., in the multiple cloning site). This results in a deletion extending from amino acid 216 to the carboxyl terminal end of prepro-TRH. To generate this deletion, pCMV-TRH was digested with ApaI, and a 6.1 kb fragment was isolated therefrom. This fragment was religated to form ΔApaI.

Transfection of cells

AtT-20 cells were transiently transfected (using Lipofectin) with 0–10 μg of pCMV-TRH, ΔBstEII or ΔApaI, and an amount of pcDNA-3 such that the total amount of transfected DNA was always 10 μg. Plasmid DNA in 1 ml of OPTI-MEM (Gibco/BRL) was mixed with 20 μg of Lipofectin reagent (Gibco/BRL) in 1 ml OPTI-MEM and the mixture was incubated for 15 minutes at room temperature. AtT-20 cells, seeded at a density of 1×10⁵ cells/well in 35 mm six-well plates, were incubated for 24 hours in DMEM containing 10% steroid-free FCS to approximately 60% confluency. Cells were washed once with OPTI-MEM and then overlaid with the transfection mixture. Incubation was continued for 6 hours at 37° C. The transfection mixture was removed and DMEM containing 10% steroid-free fetal calf serum was added to the cells which were further incubated for 18 hours at 37° C. in the presence or absence of 10 nM CRF. At the end of the incubation period, the supernatant was removed from the cells, clarified by centrifugation at 1000 g and 4° C. and then stored at 80° C. Total RNA was also isolated from each well.

For stable transfection, AtT-20 cells were plated at $2\times10^5$ cells/100 mm dish and incubated for 24 hours (approximately 40% confluency). Cells were transfected as described above with 10 μg pCMV-TRH DNA in 2 ml OPTI-MEM and 40 μg of Lipofectin Reagent in 2 ml OPTI-MEM. The transfection mix was replaced after 6 hours with DMEM plus 10% FCS. After 48 hours, the cells were trypsinized and split at a 1:6 ratio, and after a further 72 hours stably transfected cells were selected in the presence of 200 μg/ml G-418 (Gibco/BRL). After three weeks incubation in G-418, individual colonies of resistant cells were isolated and maintained in the presence of G-418.

Calcium phosphate transfection of primary anterior pituitary cells

Cells were seeded at $2\times10^5$ cells/well in 24-well plates (1 ml/well), and incubated for 48 hours in DMEM plus 10% steroid-free FCS. Fresh medium was added 3 hours prior to transfection. Cells were transiently transfected using the Gibco/BRL calcium phosphate transfection system. Each well received 0.5 ml of a $CaPO_4$-DNA precipitate formed as follows: 0.25 ml of a 10 μg DNA/250 mM $CaCl_2$ solution was added dropwise to 0.25 ml of 1×Hepes-buffered saline (1×HBS=137 mM NaCl, 21 mM Hepes, pH 7.05, 0.75 mM $Na_2HPO_4$) while bubbling air through the mixture. Precipitates were then incubated at room temperature for 20 min. After rinsing the cells with DMEM, precipitates were added to the cells and incubated at 37° C. for 8 hours. The precipitates were removed from the cells, and the cells were rinsed with DMEM and incubated for 14 hours in DMEM plus 10% steroid-free FCS.

Bioassay

The bioactivity of various synthetic peptides corresponding to the various prepro-TRH intervening sequences was assessed in AtT-20 or primary anterior pituitary cells. All experiments were conducted in triplicate. To perform this assay, AtT-20 cells were plated at a density of 105 cells/well in 24 well plates. After 24 hours, the medium was removed and replaced with steroid-free medium containing the test peptide at a concentration of $10^{-10}$–$10^{-6}$ M. When primary pituitary cultures were used, freshly dispersed anterior pituitary cells (1–2×$10^5$ cells/well) were plated in 24 well plates for 48 hours using steroid free media. Again, after 24 hours, the medium was removed and replaced with steroid-free medium containing the test peptide at a concentration of $10^{-10}$–$10^{-6}$ M. The supernatants from the cells were harvested after 4 hours of incubation under unstimulated or CRF-stimulated conditions. AtT-20 cells were stimulated with 50 nM CRF and primary pituitary cells were stimulated with 10 nM CRF. The supernatants were centrifuged and stored at $-80°$ C.

Radioimmunoassay

ACTH-like immunoreactivity was measured using an antiserum which reacts with amino acids 1–24 and 1–39 on ACTH on an equimolar basis. The assay is described in Redei et al. (1988, Endocrinology, 123:2736–2743). For these studies, $^{125}$I-ACTH 1–39 was used as a tracer. This assay is capable of detecting as little as 3 pg ACTH/tube. Intraassay and interassay coefficients of variation were 6.4% and 11.6% respectively.

Isolation of RNA and Northern Analysis

Cells were lysed using 0.75 ml Trizol (RNA isolation buffer; GIBCO/BRL). Chloroform (100 gl) was added to each sample and the mixture was placed on ice for 15 minutes whereupon the organic and aqueous phases were separated by centrifugation at 16,000 g for 20 minutes at $4°$ C. The upper aqueous phase was mixed with an equal volume of isopropanol and placed at $-20°$ C. for 1–3 hours or overnight to precipitate the RNA. Precipitated RNA was collected by centrifugation at 16,000 g for 20 minutes at $4°$ C. and the pellet was washed twice with 75% ice-cold ethanol and dissolved in 10 $\mu$l of sterile distilled water. The quantity and quality of the RNA was assessed by gel electrophoresis and by spectrophotometry.

Northern blot hybridization was performed as described (Redei et al., 1993, Endocrinology, 133:452–460). Briefly, total RNA was electrophoresed, transferred to nitrocellulose filters and was fixed thereupon by UV crosslinking. Filters were prehybridized for 3–6 hours at $42°$ C. in prehybridization buffer and were hybridized for 16 hours at $42°$ C. in the presence of a $^{32}$P-labeled probe labeled by random primer labeling. The POMC probe comprises a 923 bp fragment obtained from the plasmid pMKSU16 encoding mouse POMC DNA (Uhler et al., 1983, J. Biol. CHem. 258:257–261). Since CRF is a potent stimulator of POMC biosynthesis (Plotsky, 1991, J. Neuroendocrinol. 3:1–9), inhibition of POMC synthesis is a measure of CRIF activity. The TRH probe comprises a 1322 base pair fragment obtained from the plasmid pSP64 (Lechan et al., 1986, Science 231:159–161). Following incubation, filters were washed twice for 15 minutes each in 2×SSC/0.1% SDS at room temperature, twice for 30 minutes each in 0.1×SSC/ 0.1% SDS at $52°$ C. and were then exposed to X ray film at $-80°$ C. using intensifying screens. These filters were subsequently stripped and reprobed under similar conditions using a $^{32}$P-labeled GAPD cDNA probe. GAPD is a housekeeping gene which is used herein as a measure of the amount of sample loaded in each well of the gel. The amount of hybridization was measured by densitometry and in each case, comparison of mRNA levels were made of RNAs on the same filter. POMC mRNA levels were normalized to the amount of GAPD mRNA in each sample.

CRIF activity in Wistar and WKY rat hypothalamic extracts

To establish that AtT-20 cells respond to CRIF, hypothalamic extracts obtained from Wistar and WKY rats were fractionated by molecular weight and the appropriately sized factions were assayed for their ability to affect ACTH production in AtT-20 cells. Unstimulated ACTH levels produced by these cells served as a baseline index. Several fractions, (fraction numbers 32–34) exhibited a decrease in the basal level of secretion of ACTH. The inhibition of basal level ACTH secretion was significantly higher in cells treated with hypothalamic extract from Wistar rats (<40% of control levels) compared to WKY (60% of control levels).

Hypothalamic prepro-TRH mRNA levels in Wistar and WKY rat hypothalami were assessed by Northern hybridization analysis. The relative level of prepro-TRH mRNA (normalized to levels of β-actin mRNA) was higher in Wistar rats compared with WKY rats (0.178+0.02 vs. 0.117+ 0.03, respectively). These results establish that WKY rats, which rats hyperexpress POMC (Redei et al., 1994, Am. J. Physiol. 266:R353–R360), exhibit decreased expression of hypothalamic prepro-TRH mRNA. In addition, hypothalamic extract obtained from these rats exhibits a decreased ability to suppress ACTH secretion in AtT-20 cells. Moreover, secretion of ACTH in AtT-20 cells is decreased in response to CRIF activity.

Transfection with pCMV-TRH

Figure 2:
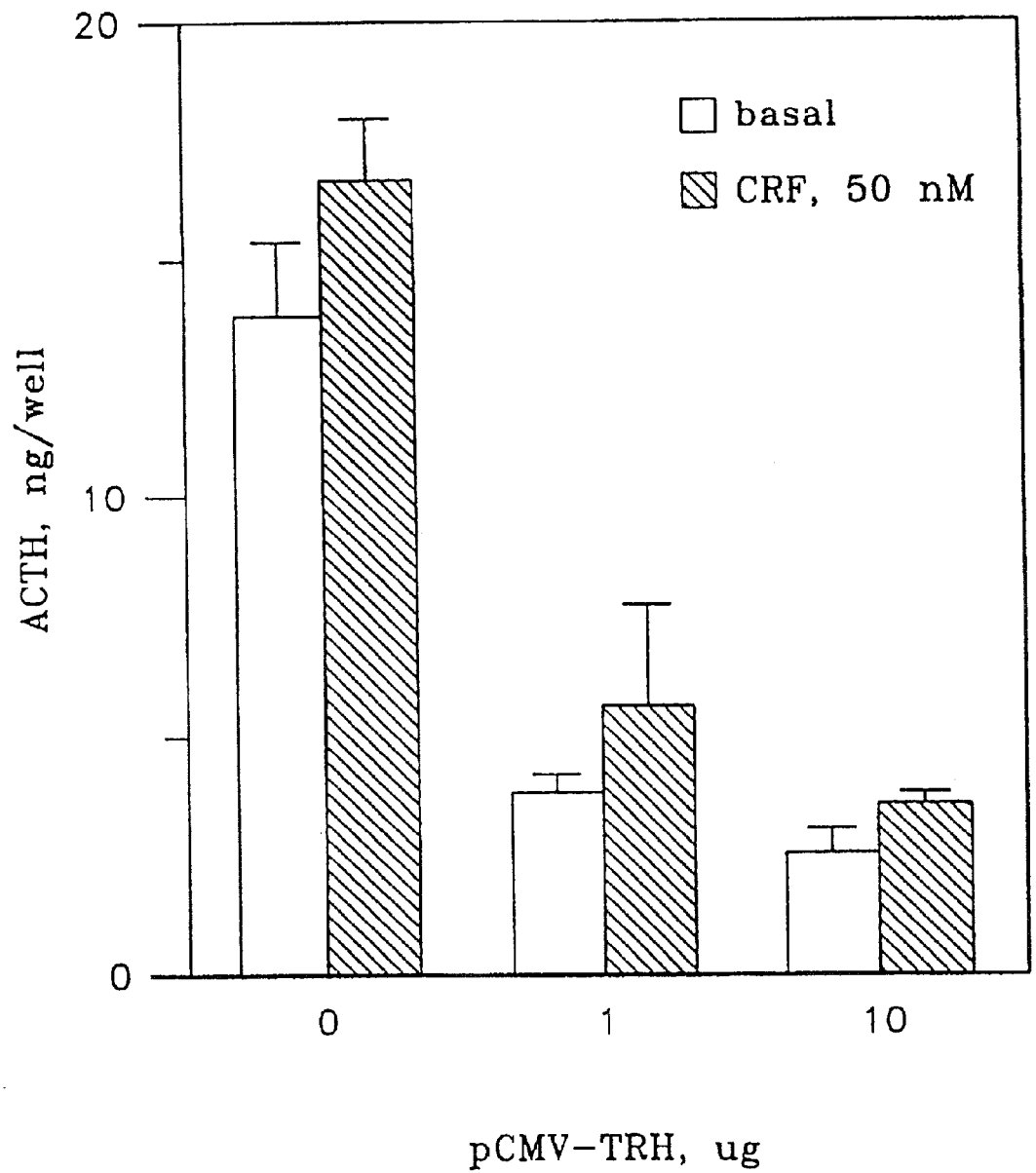
FIG. 2 is a diagram depicting basal and CRF stimulated ACTH levels in AtT-20 cells which are transfected with vector plasmid alone (0 µg) or are transfected with various concentrations of pCMV-TRH. The total amount of plasmid DNA transfected in each lane is 10 µg.

Unstimulated AtT-20 cells which were transiently transfected with the TRH expression vector pCMV-TRH, secreted reduced amounts of ACTH compared with cells which were not transfected. Surprisingly, even concentrations of DNA as low as 1 $\mu$g resulted in maximal inhibition of ACTH secretion (FIG. 2). CRF stimulated ACTH secretion was also inhibited in transfected cells (FIG. 2).

Figure 3:
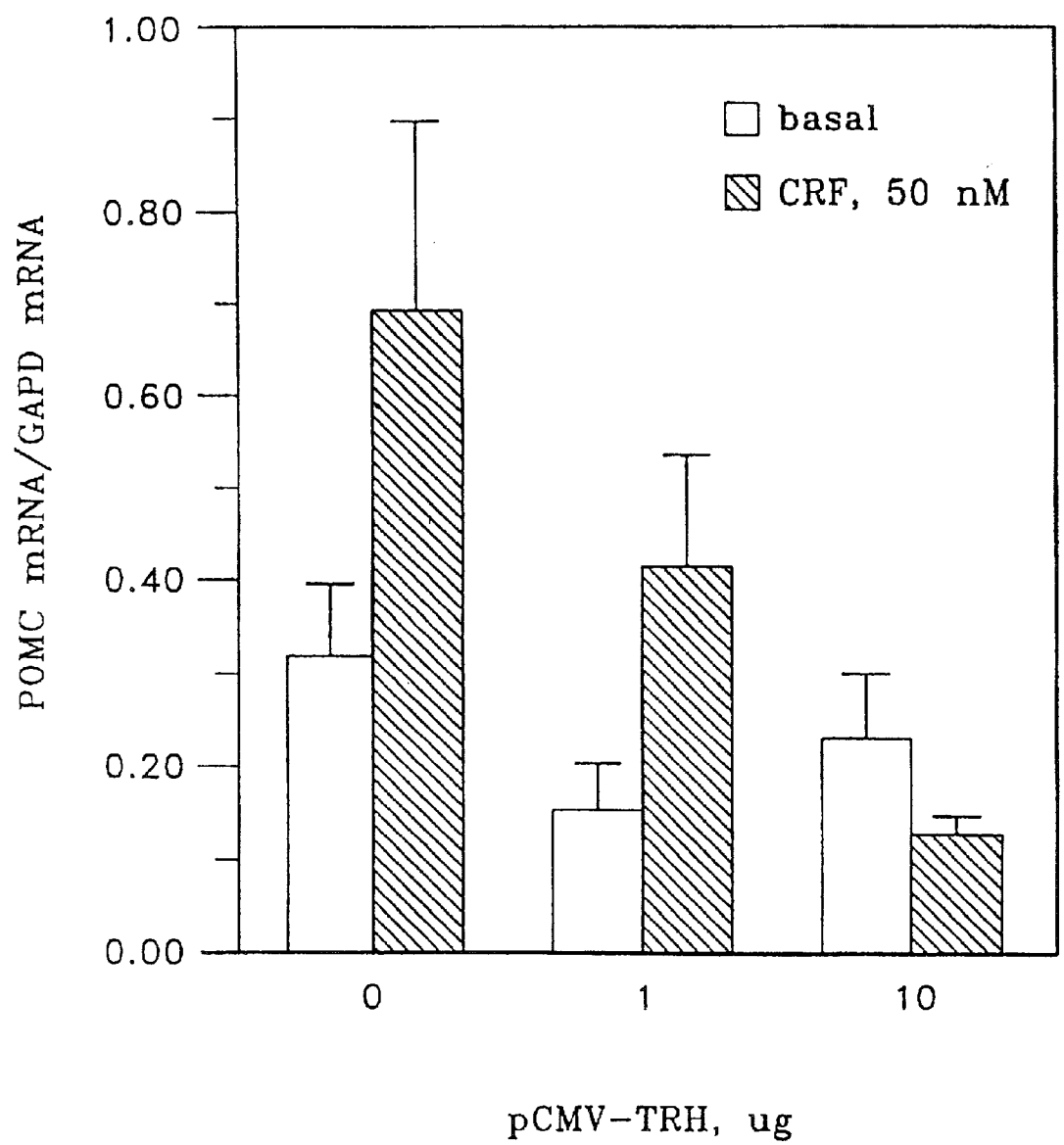
FIG. 3 is a diagram depicting the amount of POMC/GAPD (proopiomelanocortin/glyceraldehyde-3-phosphate dehydrogenase) mRNA in AtT-20 cells which are transfected with vector plasmid alone or are transfected with various concentrations of pCMV-TRH. The total amount of plasmid DNA transfected in each lane is 10 µg.

Steady state levels (either basal levels or CRF-stimulated levels) of POMC mRNA were also reduced in pCMV-TRH transfected cells as compared with untransfected control cells (FIG. 3). In yet another experiment, relative basal levels of POMC mRNA (POMC mRNA signal/GAPD mRNA signal) were 0.69+0.03 in control transfected cells, and in pCMV-TRH transfected cells these levels were suppressed in a dose-dependent manner as follows: 1 $\mu$g pCMV-TRH DNA: 0.70+0.02; 5 $\mu$g pCMV-TRH DNA: 0.52+0.05: 10 $\mu$g pCMV-TRH DNA: 0.36+0.003. CRF stimulation resulted in an increase of POMC mRNA levels to 0.82+0.04 in mock transfected cells; pCMV-TRH transfected cells exhibited somewhat reduced levels of POMC MnRNA compared with the mock transfected cell level as follows: 1 $\mu$g pCMV-TRH DNA: 0.68+0.04; 5 $\mu$g pCMV-TRH DNA: 0.63+0.13 and 10 $\mu$g pCMV-TRH DNA: 0.75+0.11, respectively.

Figure 6:
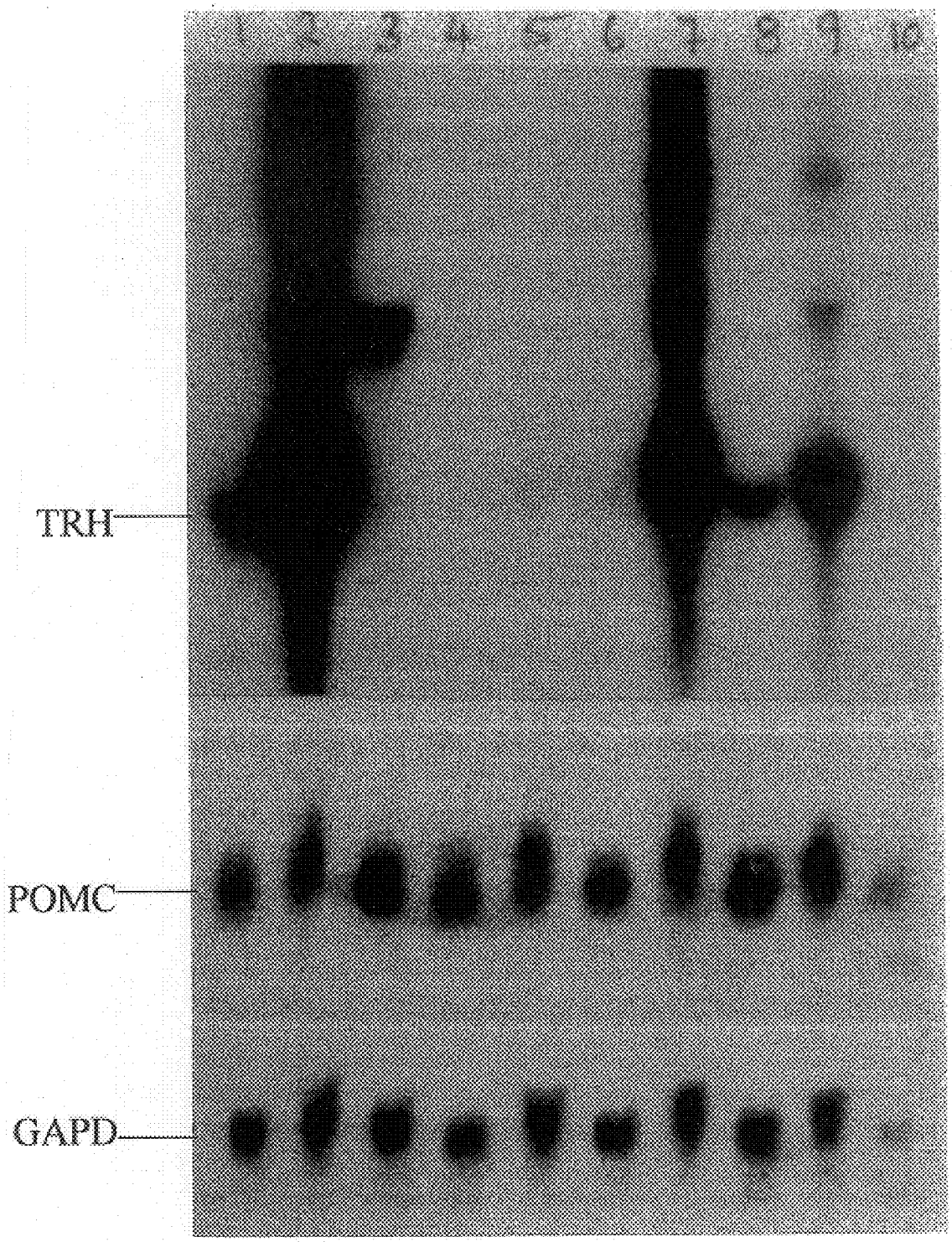
FIG. 6 is an autoradiogramn depicting Northern hybridization analysis of TRH, POMC and GAPD mRNA synthesis in AtT-20 clones stably transfected with pCMV-TRH (lanes 1–9) and in untransformed AtT-20 cells (lane 10).

Clonal cell lines stably transfected with pCMV-TRH express differing levels of prepro-TRH mRNA (FIG. 6; lanes 1–9). However, irrespective of the levels of prepro-TRH mRNA, relative levels of POMC mRNA were suppressed by 50% compared with untransfected AtT-20 cells (FIG. 6; lane 10).

Transfection of cells with ΔBstEII and ΔApaI

Figure 4A:
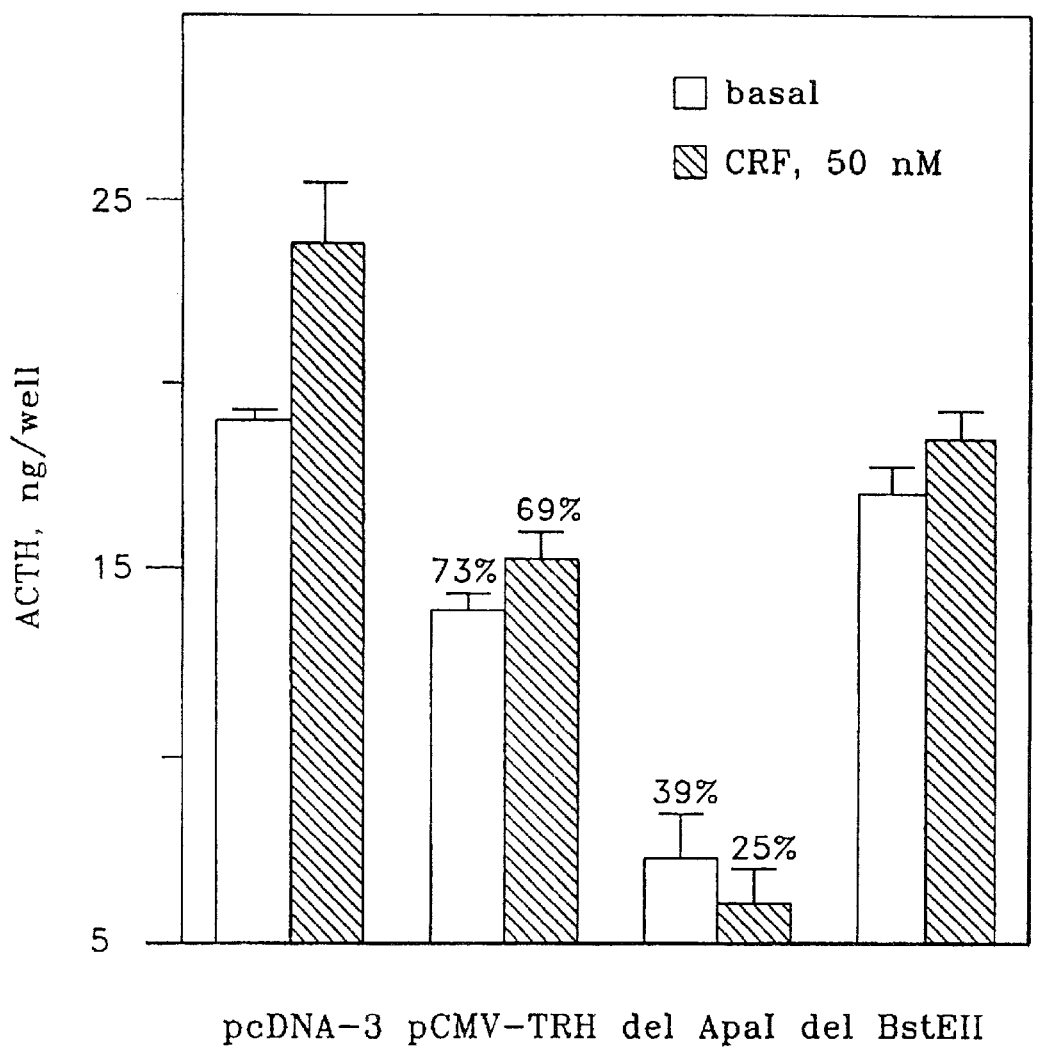
FIG. 4, comprising parts A and B, is a diagram and an autoradiogram depicting levels of ACTH and POMC produced in AtT-20 unstimulated or CRF stimulated cells which are transfected with 1 µg of vector plasmid, pcDNA3 (Invitrogen), or are transfected with 1 µg of pCMV-TRH, ΔBstEII or ΔApaI. In A, the levels of ACTH are shown. Levels of ACTH in the variously transfected cells are shown from left to right as follows: pcDNA3, pCMV-TRH, ΔBstEII, ΔApaI. In B, the amount of POMC mRNA in each type of transfected cell is shown. The control panel in this figure indicates pcDNA-transfected cells. Identical samples were loaded in each lane in each set of panels.

When deletions were made within the prepro-TRH sequence and cells were subsequently transfected with plasmids containing these deletions, CRIF activity was found to reside within the prepro-TRH 119–215 amnino acid fragment. In these experiments, unstimulated AtT-20 cells transiently transfected with 1 $\mu$g of ΔApaI exhibited decreased basal secretion of ACTH, which decrease was even more marked than that exhibited by pCMV-TRH transfected cells (FIG. 4A). In contrast, transient transfection of cells with ΔBstEII did not result in any significant decrease in basal secretion of ACTH. Furthermore, CRF stimulated ACTH secretion was reduced in cells transfected with either ΔApaI or pCMV-TRH (FIG. 4A). When levels of POMC were assessed in these cells by Northern hybridization analysis, the results were identical in that basal POMC levels were reduced in unstimulated cells transfected with ΔApaI and CRF stimulated levels of POMC were reduced in cells transfected with both ΔApaI and with pCMV-TRH (FIG. 4B).

Figure 5:
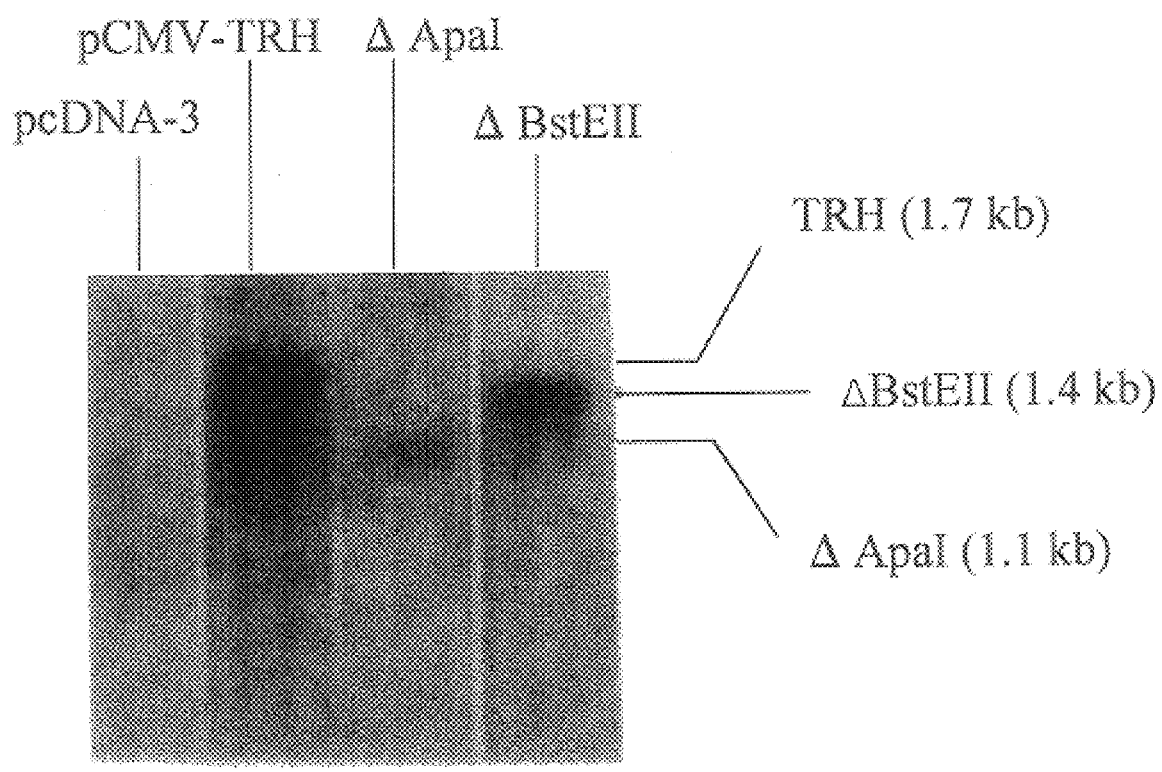
FIG. 5 is an autoradiogram depicting Northern hybridization analysis of poly A+ RNA showing TRH-specific mRNA synthesized in cells transiently transfected with control, non-TRH-containing DNA (pcDNA3), or with pCMV-TRH, ΔApaI or ΔBstEII. The size of each mRNA produced is indicated at the right of the figure.

Expression of TRH specific mRNA was assessed in AtT-20 cells which were transiently transfected with either pCMV-TRH, ΔBstEII or ΔApaI. Poly A$^+$ RNA was obtained from each set of cells and was analyzed by Northern hybridization. In each instance, mRNA of the expected size was observed as follows: Full length TRH=1.7 kb; ΔBstEII= 1.4 kb; ΔApaI=1.1 kb (FIG. 5).

Figure 7:
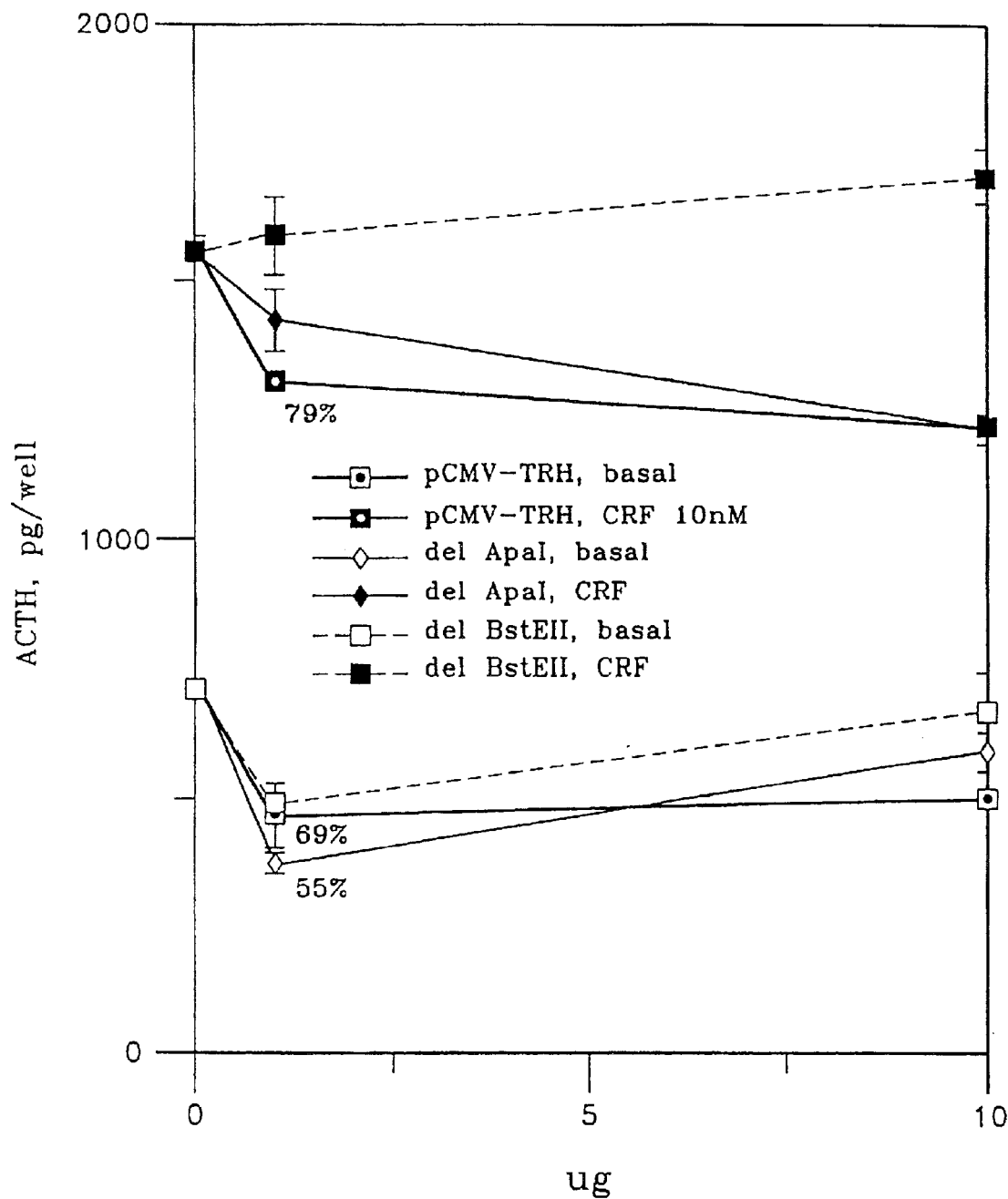
FIG. 7 is a graph depicting ACTH levels in unstimulated or CRF stimulated primary anterior pituitary cultures which are transfected with 0–10 µg of pCMV-TRH, ΔBstEII or ΔApaI, together with 0–10 µg of pcDNA3 vector, so that the total amount of plasmid DNA transfected in each lane is 10 µg.

Similar but not identical results were obtained using transiently transfected primary anterior pituitary cultures (FIG. 7). Basal ACTH secretion was reduced in primary pituitary cells which were transiently transfected with 1 μg of pCMV-TRH or with ΔApaI and to a lesser degree, these levels were also reduced in cells trans-fected with ΔBstEII deletions (FIG. 7). Secretion of ACTH was increased by approximately 100% following CRF stimulation (10 nM), which increase was reduced in cells transiently transfected with 1 or 10 μg of pCMV-TRH or ΔApaI, but not in cells transiently transfected with ΔBstEII (FIG. 7).

Assessment of CRIF activity in prepro-TRH intervening peptides

The intervening peptides of prepro-TRH (FIG. 1), i.e., those which do not comprise the mature TRH tripeptide, were examined for their ability to affect basal and CRF-stimulated ACTH secretion in AtT-20 cells. Peptides prepro-TRH 115–151, 160–169 and 178–199 were obtained from Penninsula Lab Inc. (Belmont, Calif.); peptides prepro-TRH 53–74, 83–106 and TRH precursor peptide (Lys-Arg-Gln-His-Pro-Gly-Lys-Arg) were obtained from American Peptide Co. Inc. (Sunnyvale, CA); and, peptides prepro-TRH 25–50, 208–220 and 230–255 were obtained from Quality Control QCB, Hopkington, Mass.

Figure 8:
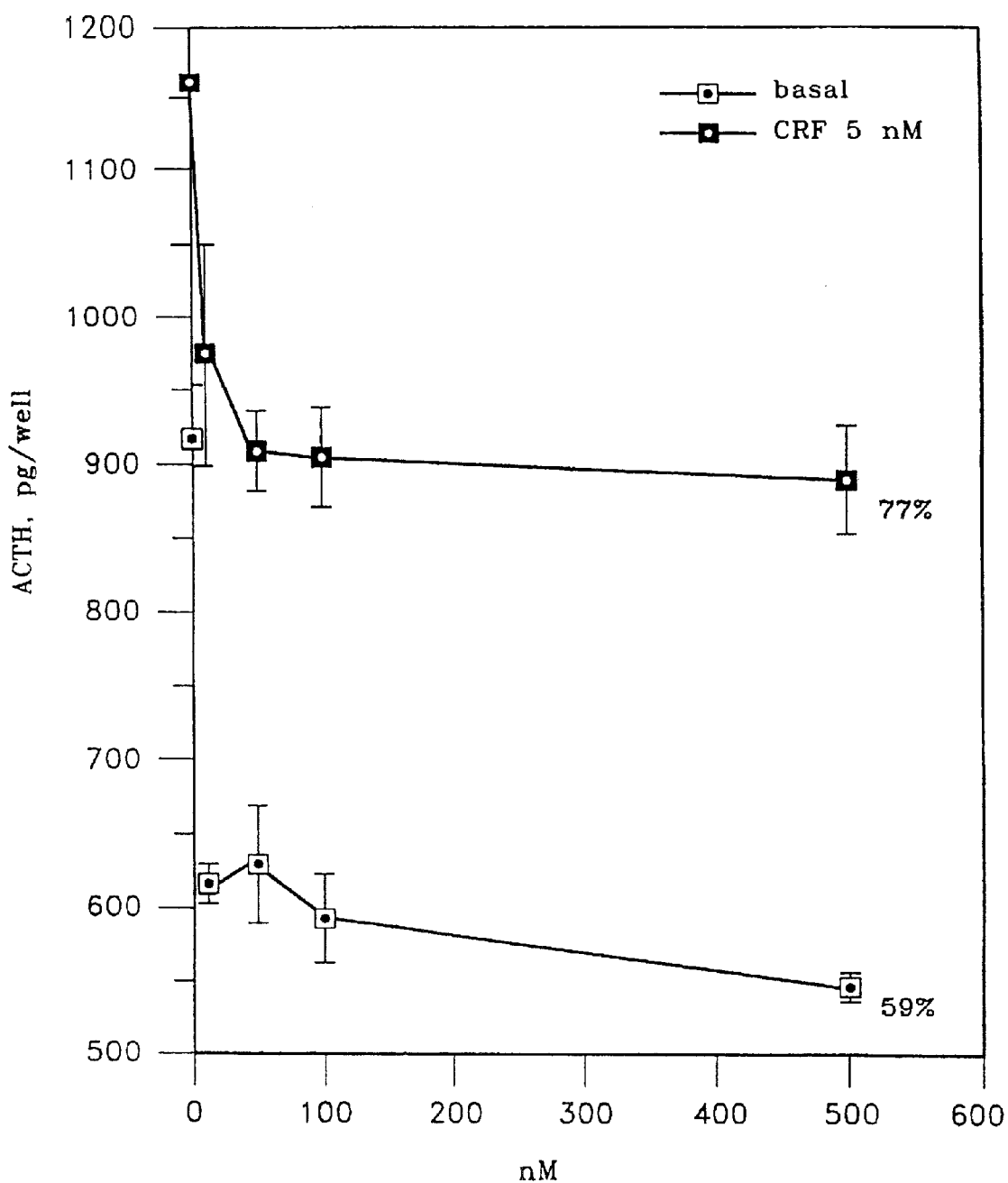
FIG. 8 is a graph depicting the effect of CRIF peptide 178–199 on the levels of ACTH in unstimulated or CRF stimulated primary anterior pituitary cells.

Peptides comprising amino acids 25–50, 53–74, 83–106, 115–151, 160–169, 178–199, 208–220 and 230–255 were individually added to AtT-20 cells and their effect on ACTH secretion was assessed. Of these peptides, only the peptide comprising amino acids 178–199 exhibited bioactivity in that both basal and CRF-stimulated ACTH secretion was reduced in their presence. Peptides comprising amino acids 178–199 and 230–250 and TRH precursor peptide were also bioassayed on primary pituitary cell cultures. In this assay, only peptide 178–199 exhibited CRIF activity in a dose response manner. The effect of peptide 178–199 on ACTH secretion in primary pituitary cultures is shown in FIG. 8.

The results of deletion studies in combination with a knowledge of the manner in which processing of prepro-TRH is known to occur, demonstrate that a peptide of amino acids 172–199, which includes the uncleaved fourth TRH portion covalently bound to the amino terminal portion of peptide 178–199, also has CRIF activity.

The results presented herein establish that a peptide residing within prepro-TRH has an inhibitory effect on both basal and CRF stimulated ACTH synthesis and secretion, which effects satisfy the requirements for CRIF activity, which peptide is therefore termed CRIF.

Figure 9:
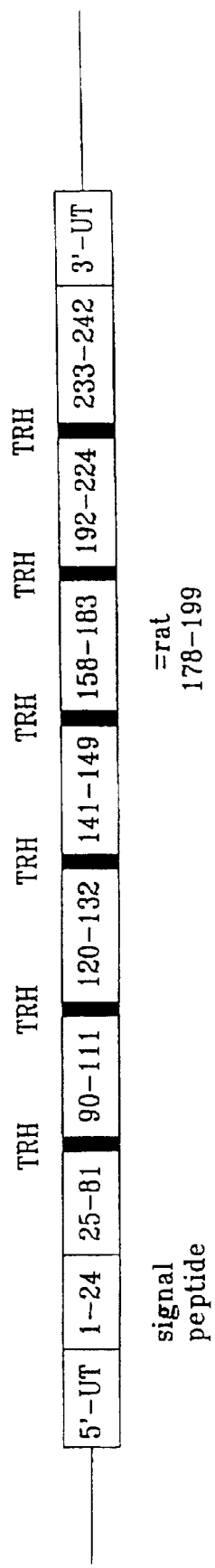
FIG. 9 is a map of the human prepro-TRH protein. Groups of amino acids are numbered beginning at the N-terminus of the molecule and the blackened areas indicate the location of each of the six mature TRH tripeptide molecules. As indicated on the figure, amino acids 158–183 in the human prepro-TRH protein correspond to amino acids 178–199 in the rat prepro-TRH protein.

A map of the human prepro-TRH protein is shown in FIG. 9, which protein shares significant similarities with the rat prepro-TRH protein (FIG. 10). In fact, rat, human and mouse prepro-TRH and in particular, that portion of prepro-TRH which constitutes CRIF, share significant homology with each other. Thus, the invention specifically includes human and mouse CRIF, in addition to rat CRIF. Given the similarities observed between rat, human and mouse CRIF sequences, and the data provided herein establishing that the activities of CRIF from these species is virtually identical, the invention must also be construed to include all mammalian CRIFs.

The fact that a corticotropin release inhibiting peptide shares a precursor with TRH suggest a new model for hypothalamic control of ACTH and TSH secretion.

According to this model, the secretion of these pituitary hormones is coupled through the influence of the two hypothalamic peptides, TRH and CRIF, produced from a single precursor molecule expressed from a gene in a discreet population of hypothalamic neurons. Because of the opposite regulatory actions of these two peptides on their respective pituitary target cells, namely that TRH stimulates pituitary thyrotrophs to secrete thyroid-stimulating hormone (TSH), while CRIF inhibits ACTH, the model predicts that TSH and ACTH levels are inversely related. Therefore, when prepro-TRH containing neurons secrete higher levels of TRH and CRIF, plasma TSH levels will be elevated and ACTH levels will be reduced. Conversely, low output of TRH and CRIF will lead to reduced plasma levels of TSH and elevated levels of ACTH. Indeed, the former situation occurs in hypothyroid states when hypothalamic prepro-TRH mRNA levels are increased (Segerson et al., 1987, Science 238:78), and the latter situation is observed when hypothalamic prepro-TRH mRNA levels are decreased in animals in a hyperthyroid state (Kakucbka et al., 1992, Endocrinology 130:2845).

Production of CRIF

To produce CRIF in large amounts, a eukaryotic cell line is transfected with a plasmid encoding CRIF wherein transcription of CRIF is placed under the control of a promoter capable of constitutively or inducibly driving expression of CRIF in the cell. The procedures for transfection are described herein and other procedures which may be used are known and are described, for example, in Sambrook et al. (1989, Molecular Cloning: A Laboratory Manual, Cold Spring Harbor, N.Y.). Constitutive promoters which may be used include the human cytomegalovirus immediate early promoter, the Rous sarcoma virus long terminal repeat promoter sequences and the like; inducible promoters include those which are induced in the presence of metal, tetracycline, or other inducers known to those skilled in the art and also described in Sambrook et al. (1989, Molecular Cloning: A Laboratory Manual, Cold Spring Harbor, N.Y.).

Preparation of a transfection vector containing the human prepro-TRH gene

The gene encoding human prepro-TRH (HTRH) cloned into pGEM-4Z was used as the starting vector (Yamada et al., 1990, Molec. Endrocrinol. 4,4, 551–557). This plasmid contains the complete prepro-TRH transcription unit, i.e., the full length gene including the promoter sequence. To prepare a vector for transfection of hTRH into AtT-20 cells, the plasmid pcDNA3 (5.4 kb) was modified as follows. The CMV promoter sequences were deleted by digestion with BglII and BamHI. The plasmid was recircularized by ligation of the resulting cohesive termini. The hTRH gene was excised from the hTRH-containing pGEM-4Z plasmid by digestion with EcoRI and was inserted into the EcoRI site of the modified pcDNA3 vector giving rise to the plasmid, pcDNA3(4.5 kb)-hTRH. This plasmid was propagated in *E. coli* MC1061 (Invitrogen).

Construction of a CRIF-minigene

A minigene having rat CRIF sequences expressing CRIF activity, which does not comprise TRH sequences was constructed as follows. A total of 227 base pairs having an 18 base pair multiple cloning restriction enzyme site positioned 5' to a 50 base pair 5' region of a preproTRH gene (wherein the first base pair is at position +1 of the prepro-TRH sequence), which is positioned 5' to 24 base pairs of preproTRH signal sequence, which is positioned 5' to 66 base pairs of CRIF coding sequence, which is positioned 5' to 9 base pairs of a translational stop codon, which is positioned 5' to an 18 base pair multiple cloning restriction enzyme sequence were ligated together using standard recombinant DNA technology. This minigene was positioned downstream from the human cytomegalovirus promoter/regulatory region within the vector pcDNA 3.

Human prepro-TRH encodes CRIF activity

To establish that the human prepro-TRH also encodes CRIF activity, a series of transfection experiments were conducted. Mouse cortitroph AtT-20 cells were either transiently or stably transfected with the human prepro-TRH gene using the transfection procedures described herein. Cells which were transiently transfected with the gene exhibited significant inhibition of both ACTH secretion and POMC expression when compared with cells which were transfected with vector alone. Furthermore, an inverse correlation between TRH gene expression and ACTH secretion was observed in cells stably transfected with human prepro-TRH.

The rat lactotroph cell line, GH3, was also stably transfected with human preproTRH to provide yet another cellular model for investigation of human CRIF activity within the human prepro-TRH gene. Given the fact that CRIF lies within prepro-TRH and must be cleaved therefrom, this cell line was chosen in order to determine the effect of the cellular processing machinery on CRIF activity. CRIF activity in GH3 cells was assessed in a bioassay designed to measure ACTH secretion using AtT-20 cells as a target. The results of these experiments are described below.

Conditioned medium obtained from GH3 cells stably transfected with human prepro-TRH suppressed ACTH secretion in AtT-20 cells. In contrast, conditioned medium obtained from mock-transfected cells (i.e., cells transfected with vector alone) had no effect on ACTH secretion in AtT-20 cells. In addition, GH3 cells which were transfected with human prepro-TRH responded to $T_3$ treatment at a concentration of 1–100 nM by suppressing expression of TRH mRNA. These data therefore establish that expression of preproTRH and subsequently secretion of ACTH, may be regulated in cells having thyroid hormone receptors.

Figure 11B:
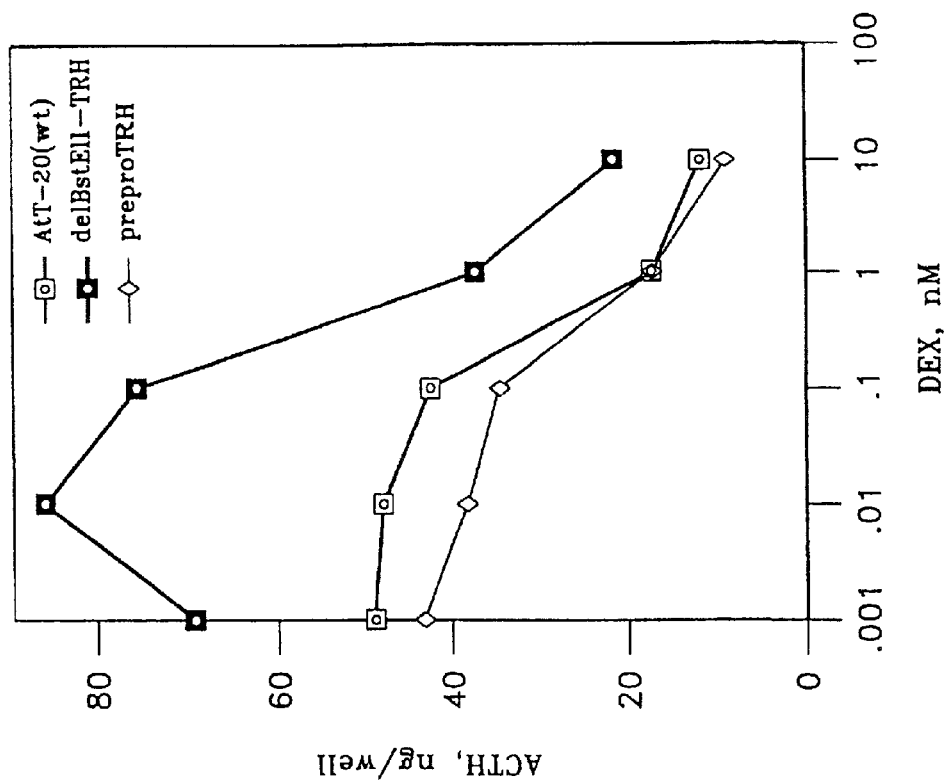
FIG. 11, comprising parts A and B, is a series of graphs depicting secretion of ACTH in untransfected AtT-20 cells or in cells transfected with prepro-TRH (A) or ΔBstEII (B), to which cells was added dexamethasone.

The effect of dexamethasone on ACTH secretion in AtT-20 cells stably transfected with rat prepro-TRH or with ΔBstEII Cells which are stably transfected with prepro-TRH cDNA and are therefore continuously producing prepro-TRH 178–199 should exhibit an increased inhibition of ACTH secretion following dexamethasone treatment. To confirm that this is the case, untransfected AtT-20 cells and a clone of rat prepro-TRH stably transfected AtT-20 cells, which clone exhibited high levels of expression of prepro-TRH, were seeded into wells at a concentration of 5×105 cells/ml of DMEM and 10% fetal calf serum. Cells were washed and treated with dexamethasone (DEX) at concentrations of 1, 10, 100 or 1000 nM for 24 hours in medium supplemented with 10% steroid-free fetal calf serum. The supernatant was harvested and the amount of ACTH contained therein was measured and the results are presented in FIG. 11.

Figure 11A:
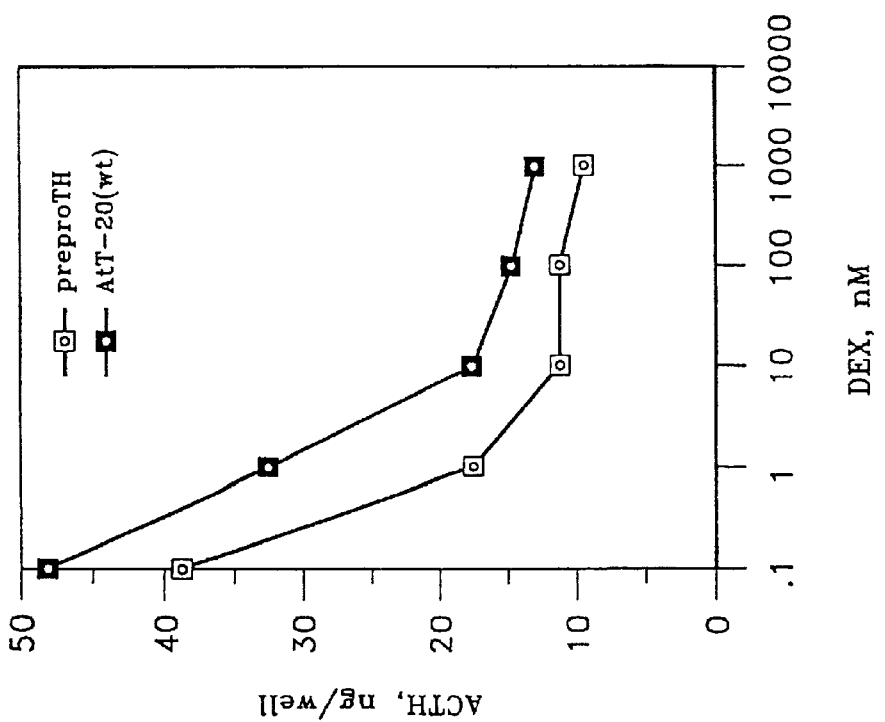

Although the basal levels of ACTH secretion were lower in prepro-TRH transfected cells than in untransfected cells, treatment with DEX suppressed ACTH secretion in both untransfected and in transfected cells in a dose response manner. However, DEX treated transfected cells exhibited a higher level of inhibition of ACTH secretion than did untransfected cells and this inhibition was most marked at lower concentrations of DEX (FIG. 11A). This experiment was repeated using less cells per well (5×104 cells/well) with essentially the same results. In contrast to the above, cells which were transfected with ΔBstEII exhibited no inhibition of ACTH secretion following treatment with low concentrations of DEX. Thus, DEX-induced inhibition of ACTH secretion of prepro-TRH transfected cells reflects the additional inhibitory effects of constitutively secreted prepro-TRH 178–199 on ACTH secretion.

The effect of CRIF on the development of rheumatoid arthritis

The data presented below establish that CRIF contributes to the development of rheumatoid arthritis (RA) by diminishing the activity of the HPA axis.

RA is an autoimmune disease characterized by chronic degradation of the joints resulting from inflammation of synovial membranes. SCW-induced inflammation in the autoimmune prone female Lewis rat is an accepted animal model for the study of RA. In this animal, susceptibility to the inflammatory response is greatly enhanced by the fact that it has a defective HPA axis and low glucocorticoid levels. It is likely that increased thyroid activity decreases the susceptibility to inflammatory immune disease by increasing glucocorticoid levels. The discovery of CRIF encoded within the same precursor as TRH establishes a direct link between the HPA and thyroid axes. Thyroid hormones may play a fundamental role in regulating the HPA axis by modulation of levels of prepro-TRH mRNA. In fact, thyroxin ($T_4$) treatment decreases the adverse inflammatory effects of SCW-induced autoimmune responses (Rittenhouse et al., 77$^{th}$ Endocrine Society Meeting, 1995).

To determine the role played by thyroid hormones and concomitant changes in the HPA axis in the development of SCW-induced inflammatory response, expression of genes which reflect the status of thyroid function (TRH), pituitary-adrenal activity (POMC) and inflammation (IL-1β and MIP-1α, a macrophage specific inflammatory protein) was measured. Adult female rats were fed a regular diet (control), or a regular diet plus 0.012% $T_4$ (hyperthyroid) or 0.05% 6-propyl-thiouracil (PTU) supplied in the in drinking water (hypothyroid), for seven weeks. A preparation of SCW (20 μg/g of body weight) was administered intraperitoneally to the rats three days before decapitation. Anterior pituitary POMC, hypothalamic TRH and peritoneal macrophage IL-1β and MIP-1α mRNA levels were assessed by Northern blot hybridization analysis using specific cDNA probes. The levels of mRNA were normalized to the housekeeping gene, GAPD, and were quantified by image analysis densitometry. Plasma levels of TSH and CORT were determined by RIA. The results are presented in FIG. 12.

Figure 12B:
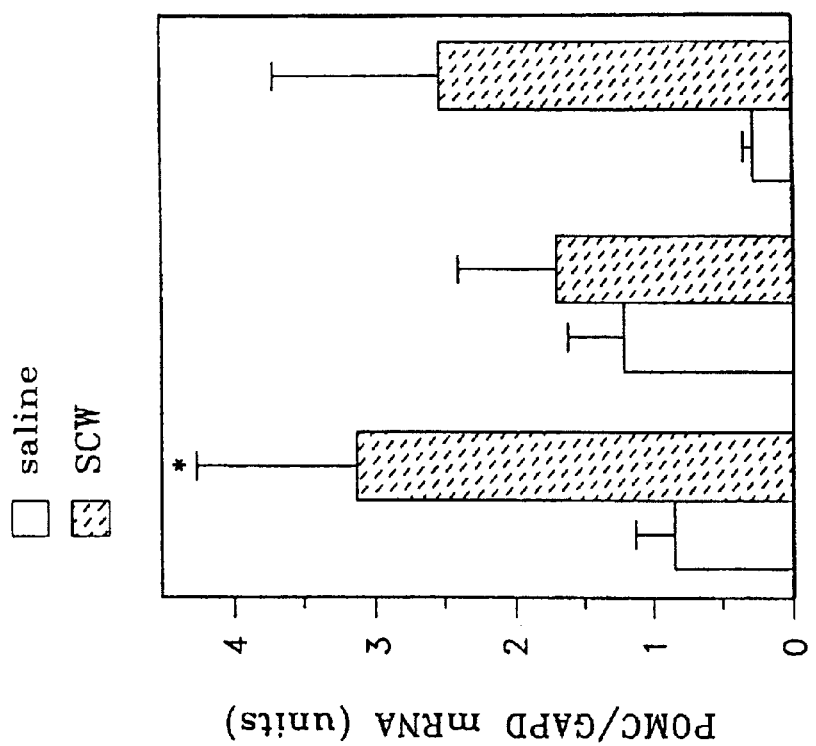
FIG. 12, comprising parts A, B, C, D and E, is a series of graphs depicting expression of TRH/GAPD mRNA (A), POMC/GAPD mRNA (B), MIP1α mRNA (C) and IL-1β mRNA (D) and, production of plasma corticosterone steroid hormone (E) in control rats or in hypo- or hyperthyroid rats, following administration of streptococcal cell wall (SCW) preparation.
Figure 12A:
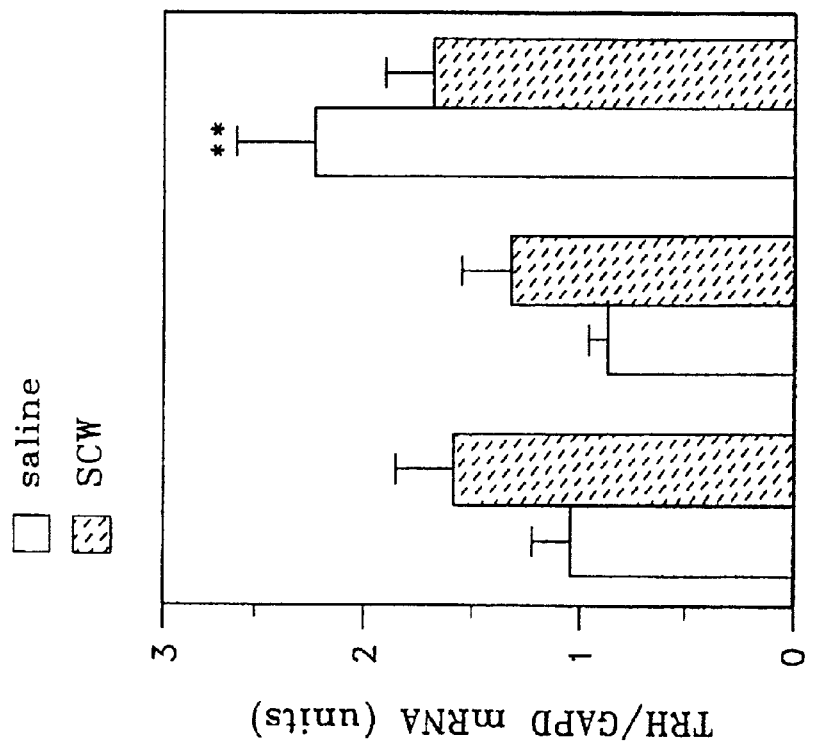

The levels of TRH mRNA were decreased by 20% in the hyperthyroid group of animals and were increased by 52% ($p<0.01$) in the hypothyroid group (FIG. 12A). Injection of SCW resulted in an increase in TRH mRNA levels in control and hyperthyroid rats and in a decrease in TRH mRNA levels in hypothyroid rats. In contrast, each of the groups of rats exhibited the opposite pattern with regard to levels of POMC mRNA in response to altered thyroid status (FIG. 12B). This is indicative of increased pituitary adrenal activity in hyperthyroid and decreased pituitary adrenal activity in hypothyroid rats and suggests a direct connection between the HPA and thyroid axes.

Figure 12D:
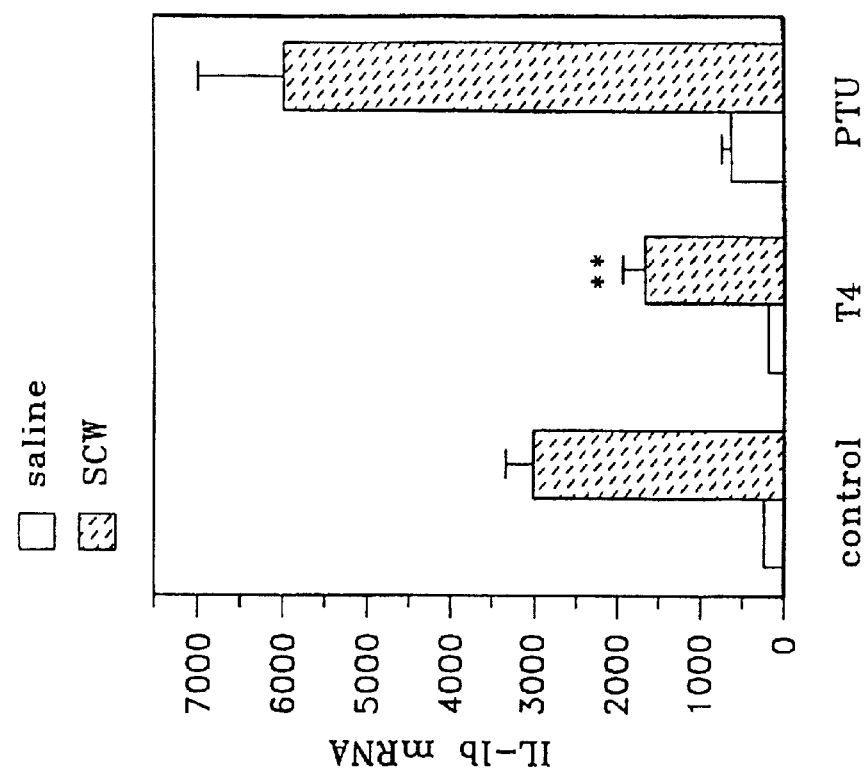
Figure 12C:
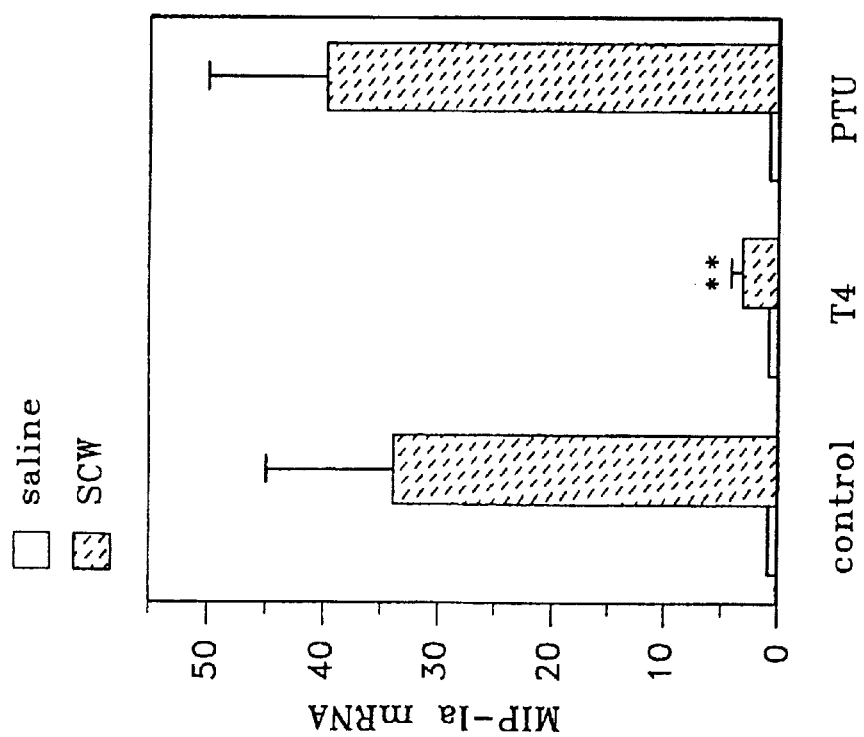
Figure 12E:
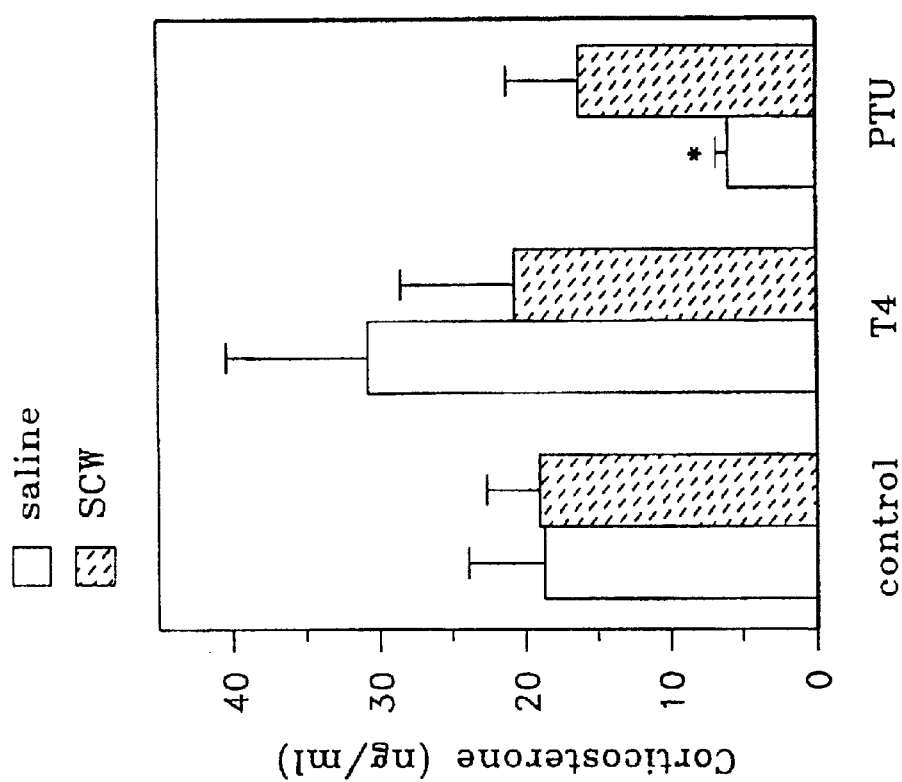
Figure 13B:
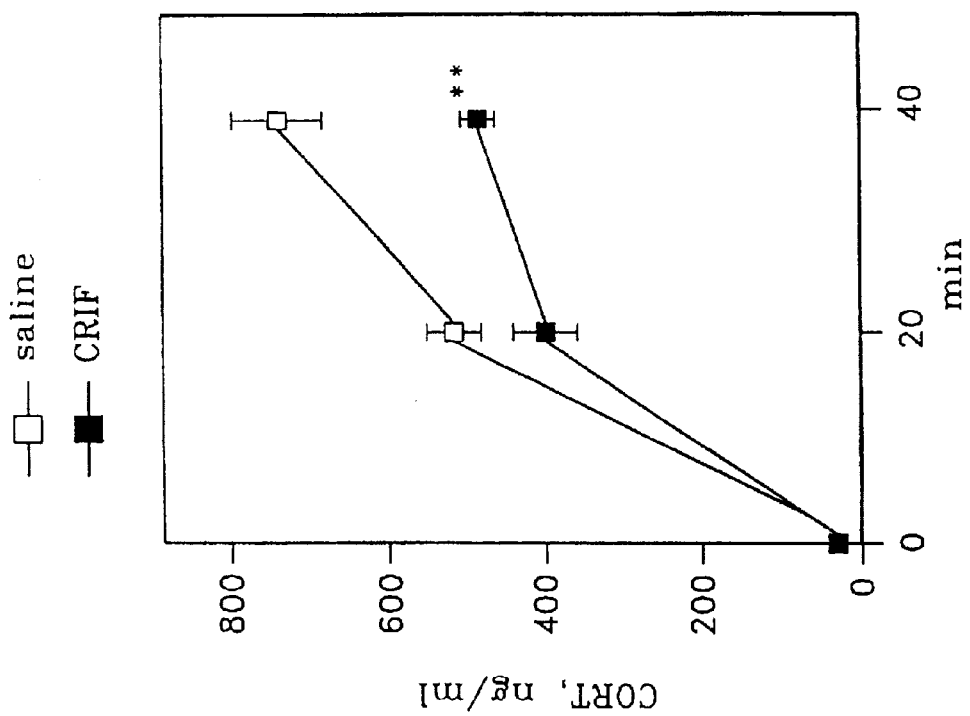
FIG. 13, comprising parts A, B, C and D, is a series of graphs depicting the in vivo corticosterone response and anti-depressant effects of CRIF in rats undergoing the Porsolt swim test and which have been administered CRIF. (A) resting rats; (B) swim-stressed rats; (C) floating time in swim-stressed rats; and, (D) struggling time in swim-stressed rats.
Figure 13A:
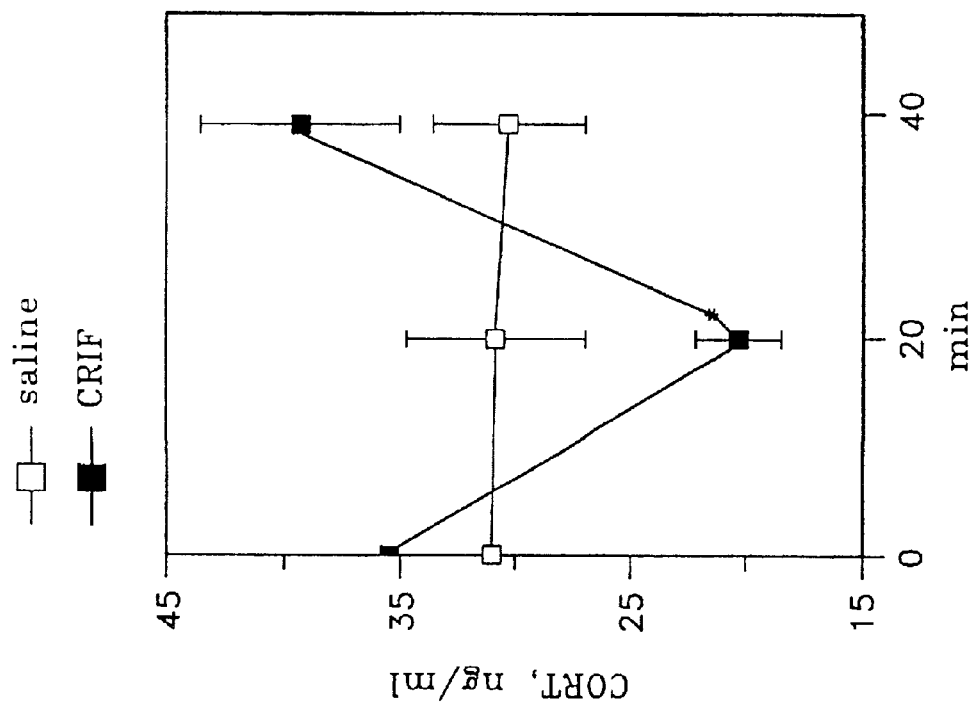
Figure 13D:
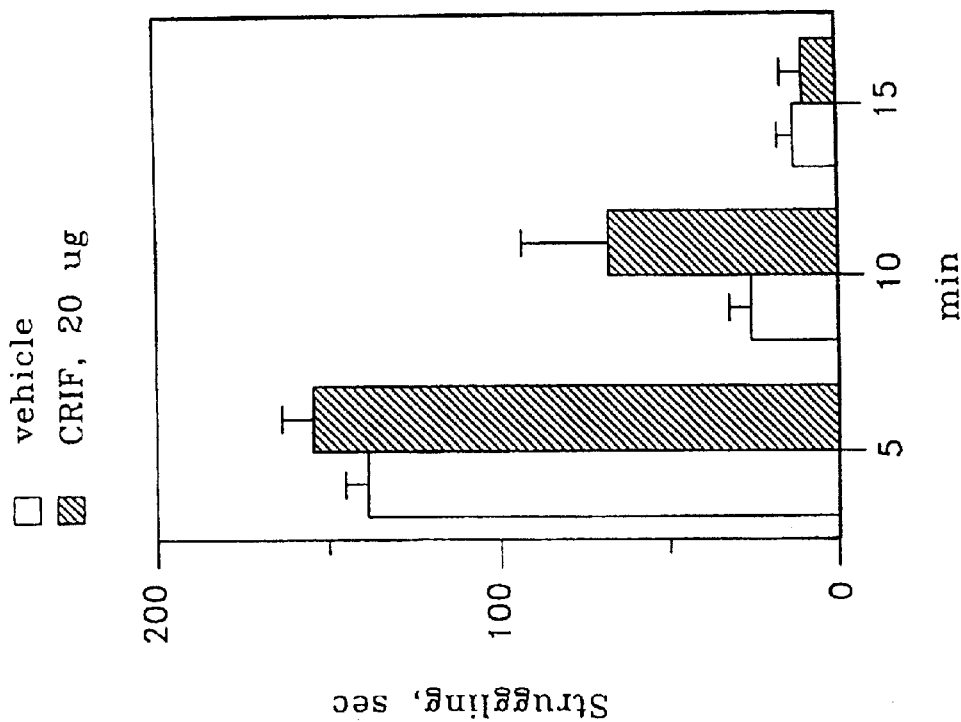
Figure 13C:
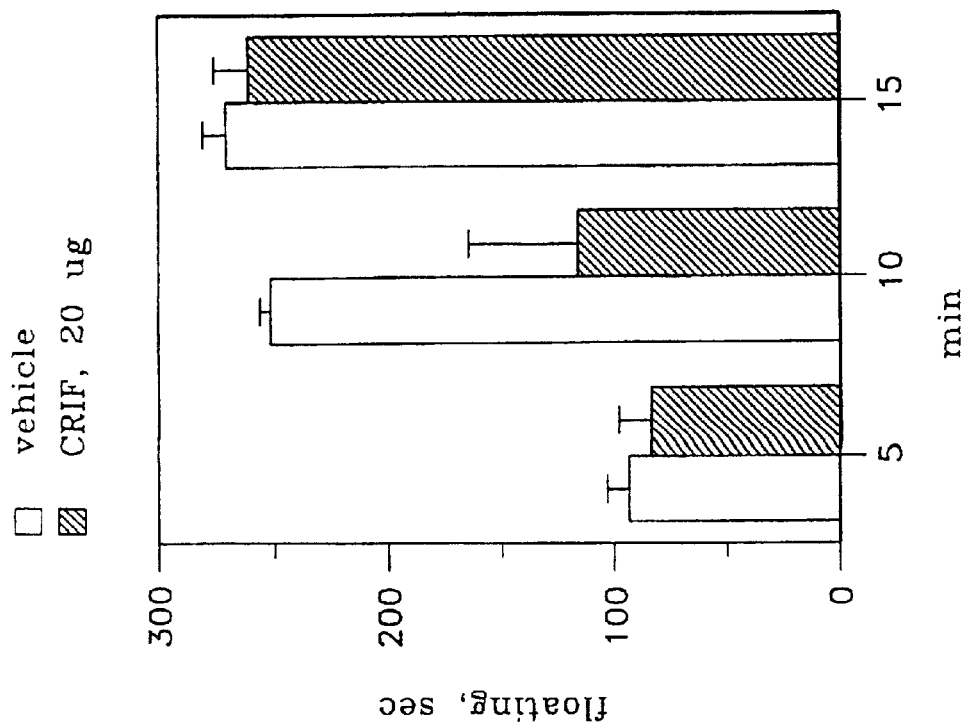

When presented with an inflammatory insult (i.e., SCW), macrophages become activated and secrete an array of cytokines such as MIP-1α and IL-1β. In control non-SCW-administered rats, MIP-1α was not detected in macrophages whereas in SCW-administered control rats, a dramatic (17-fold) induction of MIP-1α mRNA was observed (FIG. 12C). When hypothyroid rats were administered SCW, an even greater (22-fold) increase in MIP-1α mRNA levels was observed, whereas hyperthyroid rats exhibited only a 1.7-fold increase in MIP-1α levels when administered SCW. A similar pattern of expression of IL-1β was observed in untreated and SCW-treated rats (FIG. 12D). These data establish that the hypothyroid state exacerbates while the hyperthyroid state diminishes the inflammatory effects of SCW. Hypothyroid rats exhibited a significant decrease in plasma CORT levels and hyperthyroid rats exhibited a significant increase in plasma CORT levels (FIG. 12E). These latter results reflect the endogenous glucocorticoid milieu. To confirm the thyroid status of the rats, plasma levels of TSH were measured and were correlative of the expected thyroid status of each of the different groups of rats.

The data just provided establish that a CRIF antagonist may be used to treat an animal having an inflammatory disease to alleviate or abate that disease. These data further establish that either of $T_3$ or $T_4$ may be administered in the absence of a CRIF antagonist and have the same effect, i.e., administration of $T_3$ or $T_4$ in the absence of a CRIF antagonist may also reduce the severity of or even abate inflammatory disease in an animal.

Inhibition of basal and swim-stress induced CORT in rats treated with CRIF in vivo To assess the ACTH release inhibitory activity of prepro-TRH 178–199 in vivo, 20 μg of prepro-TRH 178–199 was administered intravenously into freely moving Wistar rats under resting conditions and immediately prior to forced swim stress. Prior to administration, a vascular access port was implanted in the rats, which port was connected to a catheter inserted into the right jugular vein (Redei et al., 1994, Neuroendocrinology 60:113–123). Two days following implantation, the rats were provided with a 2 hour acclimatization period and a basal blood sample of 0.5 ml was obtained through an extender connected to the port. The rats were then administered 20 μg of CRIF in a 100 μg/ml solution of saline. The rats were divided into groups. Additional blood samples were obtained at 20 and 40 minutes following administration of CRIF or vehicle from one group of rats which were undisturbed. A second group of animals were forced to swim for 15 minutes in 25° C. water, they were dried and were returned to their cages. Blood samples were also obtained from these rats at 20 and 40 minutes from the time at which the swim stress was initiated. Plasma ACTH and CORT levels were determined in each of the samples by RIA.

The CORT response to CRIF administration in resting (A) and stressed (B) rats is shown in FIG. 13, parts A and B. Administration of CRIF inhibited, to a significant degree (p<0.01), both resting and stress-induced CORT levels in the rats. Further, CRIF administration effected a decrease in the time the rats spent floating (FIG. 13C) and increase in the time the rats spent struggling (FIG. 13D) in the second 5 minutes of the 15 minute Porsolt swim test, suggesting that CRIF effects a decrease in depressive behavior.

Figure 14B:
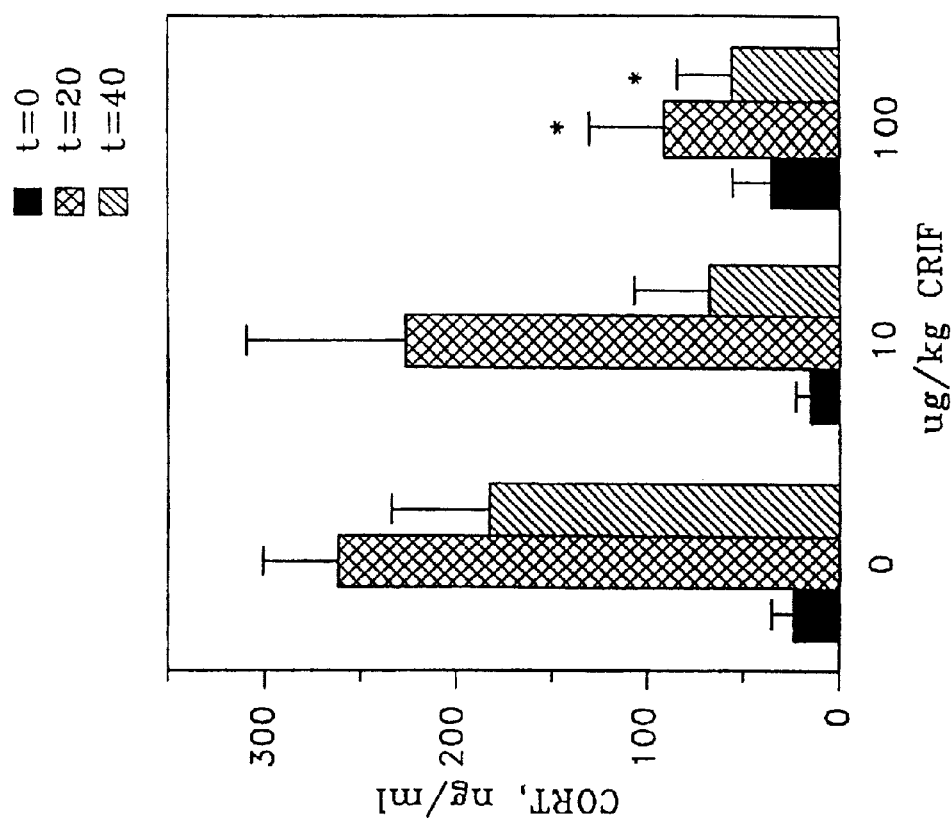
FIG. 14, comprising parts A and B, is a series of graphs depicting inhibition of ACTH and corticosterone response in vivo in rats exposed to footshock stress following administration of different doses of CRIF. (A) measurement of ACTH levels; (B) measurement of corticosterone levels.
Figure 14A:
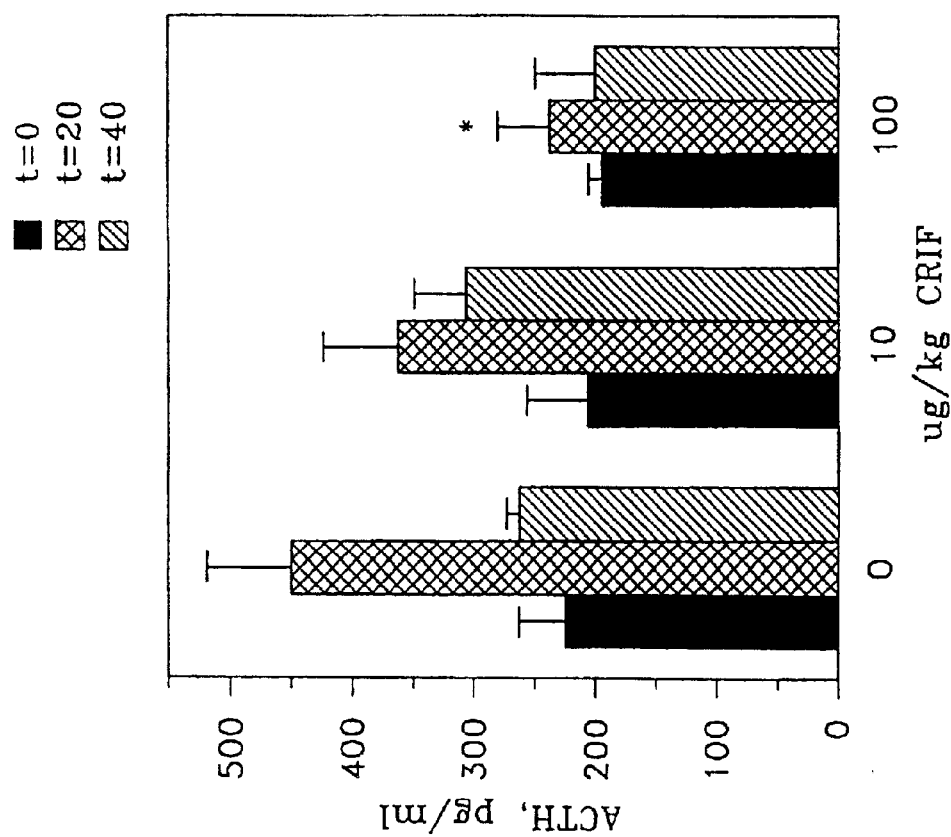

Inhibition of ACTH and CORT response to footshock stress in rats treated with CRIF in vivo Increasing amounts of prepro-TRH 178–199 were administered to freely moving adult male Wistar rats (300–350 g) prior to exposure to intermittent footshock stress using the experimental protocol similar to that described above. The animals were cannulated as described and two days later they were subjected to intermittent footshock stress (0.2 mA, 15 seconds, 0.5 seconds on and 0.5 seconds off) immediately following intravenous administration of saline or of increasing amounts of prepro-TRH 178–199. Resting (non-shocked) animals also served as controls. Blood samples were obtained as described and plasma levels of ACTH and CORT were assessed in the same. The results are presented in FIG. 14. Plasma levels of ACTH were significantly reduced in stressed animals which had been administered CRIF (FIG. 14A). Inhibition of plasma CORT levels by prepro-TRH 178–199 was even more marked than inhibition of ACTH and was evident even at lower doses of prepro-TRH 178–199 (FIG. 14B).

Restraint Stress produces region specific changes in rat brain CRIF

The data now presented establish that the concentration of CRIF in rat brain is altered in specific regions of the brain in response to stress.

A specific radioimmunoassay was developed having a sensitivity of 19 pg/tube using a polyclonal antibody and $^{125}$I-Tyrosine$^{178}$-CRIF as a tracer. The polyclonal antibody was generated following immunization of rabbits with CRIF conjugated to bovine serum albumin. $^{125}$I-Tyrosine-CRIF was obtained using the chloramine-T method. Since Tyrosine-CRIF is bioactive in AtT20 cells (i.e. exhibited CRIF activity in these cells), $^{125}$I-Tyrosine-CRIF is predicted to be biologically active in AtT20 cells. Thus, $^{125}$I-Tyrosine-CRIF is also useful for isolation of a CRIF receptor using standard receptor binding assays.

Particular regions of the rat brain were dissected from adult male rats (n=6 per group) at either 9:00 am or 9:00 pm at 30, 90 and 180 minutes following thirty minutes of restraint stress. The amount of CRIF in each region of the brain was measured using the above described radioimmunoassay.

CRIF (ng/mg of total protein) was found in different regions of the brain in the following concentrations: Hypothalamus 9.2; septum 6.3; caudate 2.9; amygdala 0.82; prefrontal cortex 0.75; and periaquaductal grey (PAG) 0.6. The highest amount of CRIF was found in the median eminence (ME) being present at a concentration about five-fold greater than that found in the hypothalamus. A negligible amount of CRIF was found in several other brain tissues tested. A diurnal morning decrease of CRIF was observed in the ME, pituitary and septum; however, CRIF was increased in PAG in the morning.

Following stress, change in CRIF content in specific regions of the brain was observed ($F_{[5,16]}$=1.98, p<0.05). At 30 minutes, a small increase in CRIF concentration was observed in the hypothalamus, septum, caudate and amygdala followed by a decrease in the hypothalamus, caudate and amygdala at 90 and 180 minutes post-stress. In the prefrontal cortex and PAG, CRIF concentrations were decreased in response to stress in the absence of any initial increase. In contrast, CRIF concentrations were increased in the ME and pituitary at all times examined post-stress.

These data establish that the radioimmunoassay described herein provides an efficient test for measurement of CRIF in brain. The data also establish that CRIF concentrations in brain vary in different regions of the brain following the application of stress.

The effect of CRIF on prolactin secretion

Figure 15A:
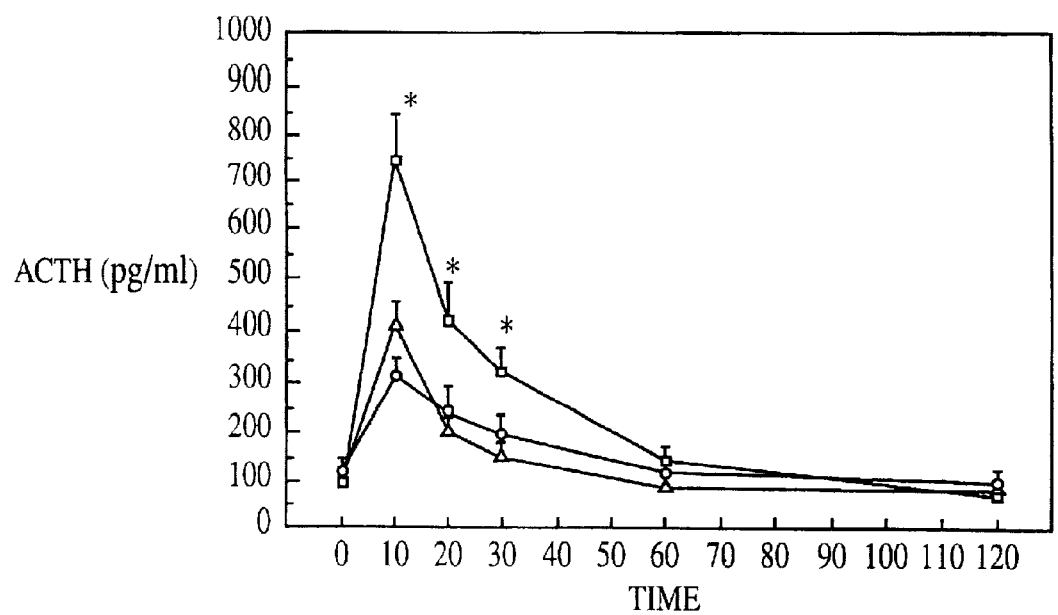
FIG. 15, comprising parts A, B and C, is a series of graphs depicting the in vivo effects of CRIF on ACTH, corticosterone and prolactin levels in rats which were subjected to restraint stress. Animals were injected intravenously (iv) with CRIF or the vehicle 5 minutes prior to the restraint period. Serial blood samples were obtained at 10, 20, 30, 60 and 120 minutes following stress onset. (A) ACTH, (B) corticosterone (CORT) and (C) prolactin (PRL) levels were measured by radioimnmunoassay.
Figure 15B:
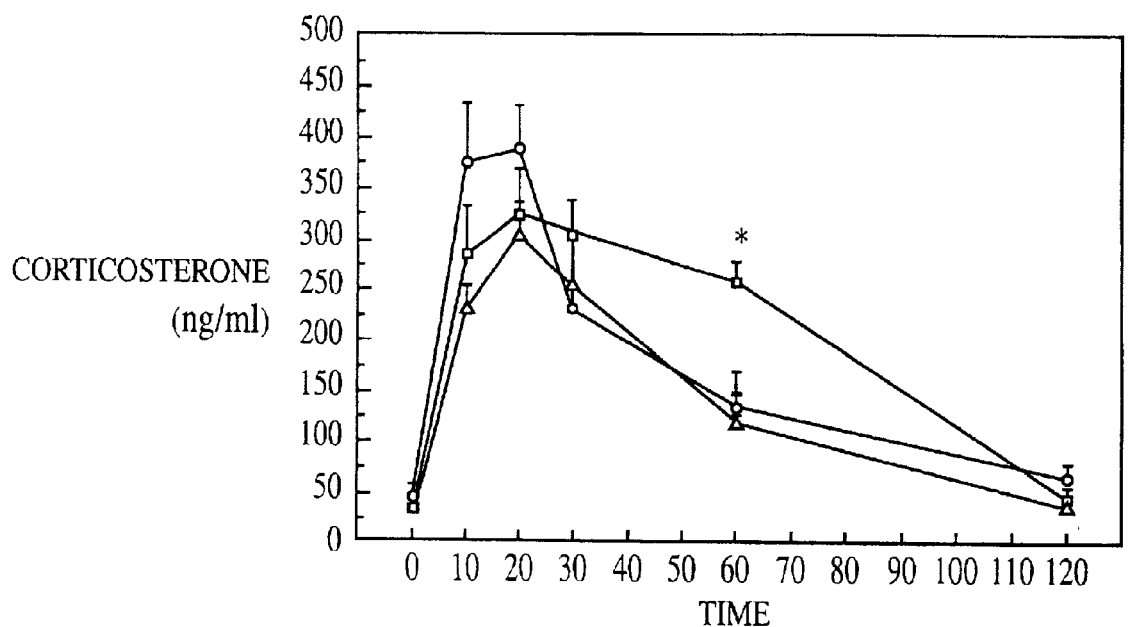
Figure 15C:
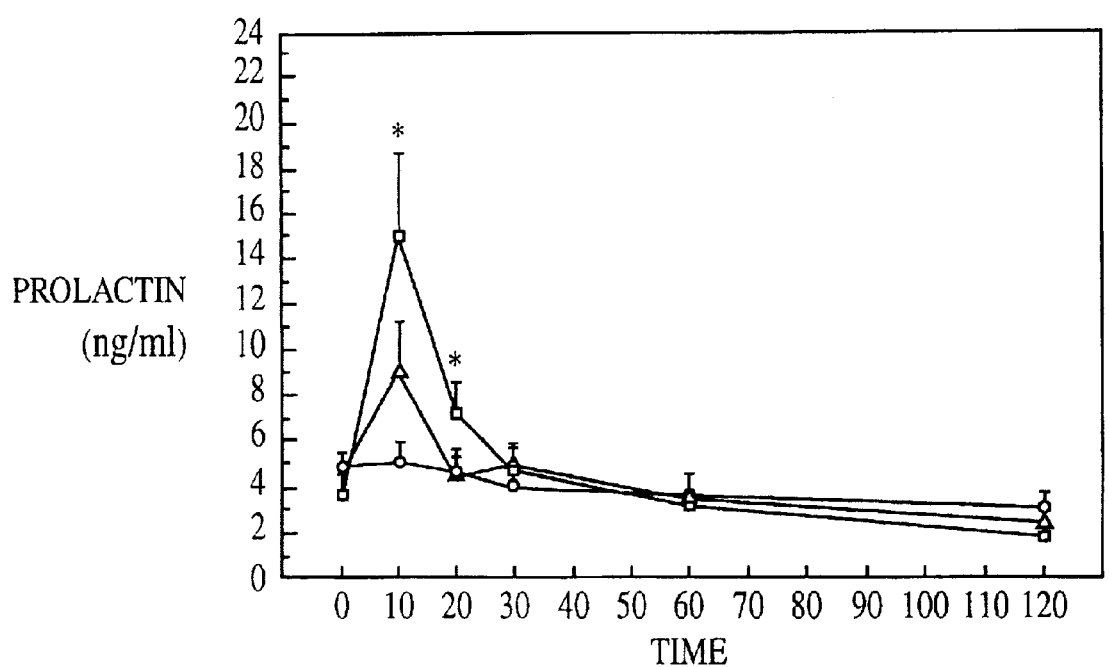

The ability of CRIF to inhibit stress-induced hormone secretion was examined in rats exposed to restraint stress for 5 minutes. Animals were injected intravenously (iv) with CRIF or the vehicle in the absence of CRIF 5 minutes prior to the restraint period. Serial blood samples were obtained at 10, 20, 30, 60 and 120 minutes following the onset of stress. ACTH, corticosterone (CORT) and prolactin (PRL) levels were measured by radioimmunoassay (Van de Kaar et al., 1982, Neuroendocrinology 35:225–230). Following iv administration, CRIF significantly inhibited the stress-induced rise in ACTH, CORT and PRL (FIGS. 15A, B and C). CRIF administration did not influence basal prolactin secretion, indicating that its effects are not due to an increase in dopaminergic tone. Thus, CRIF has a marked affect on secretion of prolactin and therefore may be used to treat diseases associated with increased secretion of prolactin.

Behavioral effects of in vivo administered CRIF

Figure 16A:
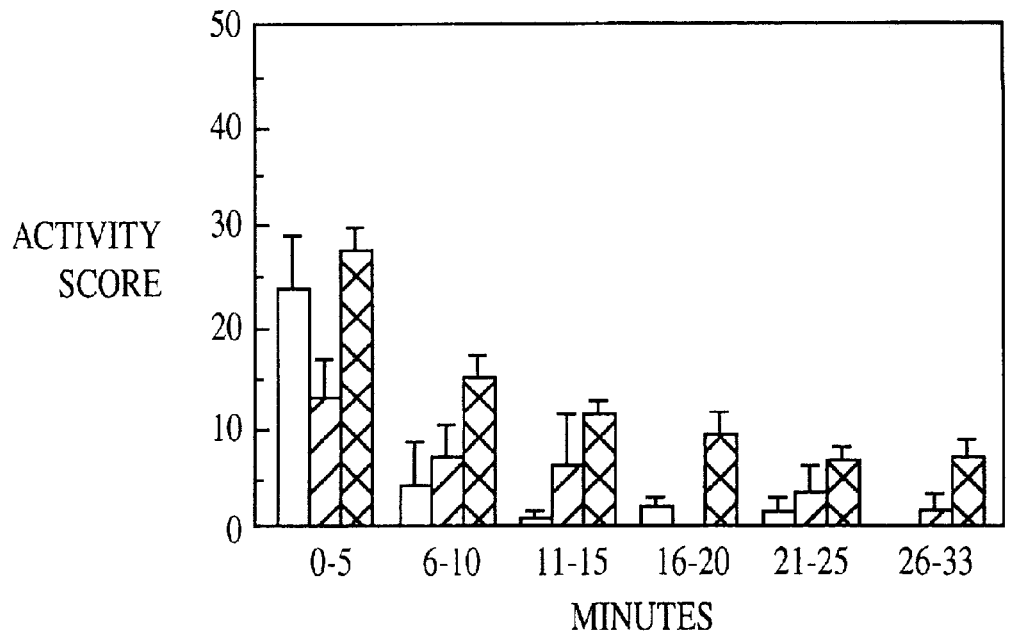
FIG. 16, comprising parts A, B, C and D, is a series of graphs depicting the effects of CRIF on the behavior of rats in vivo in an open field test. The animals were placed in the center of a 15 inch diameter open-field 5 minutes following intracerebroventricular (icv) administration of CRIF. The subsequent behavior of the animals was videotaped for a 30 minute period. (A) activity; (B) active sniffing; (C) grooming; and (D) rearing, were measured.
Figure 16B:
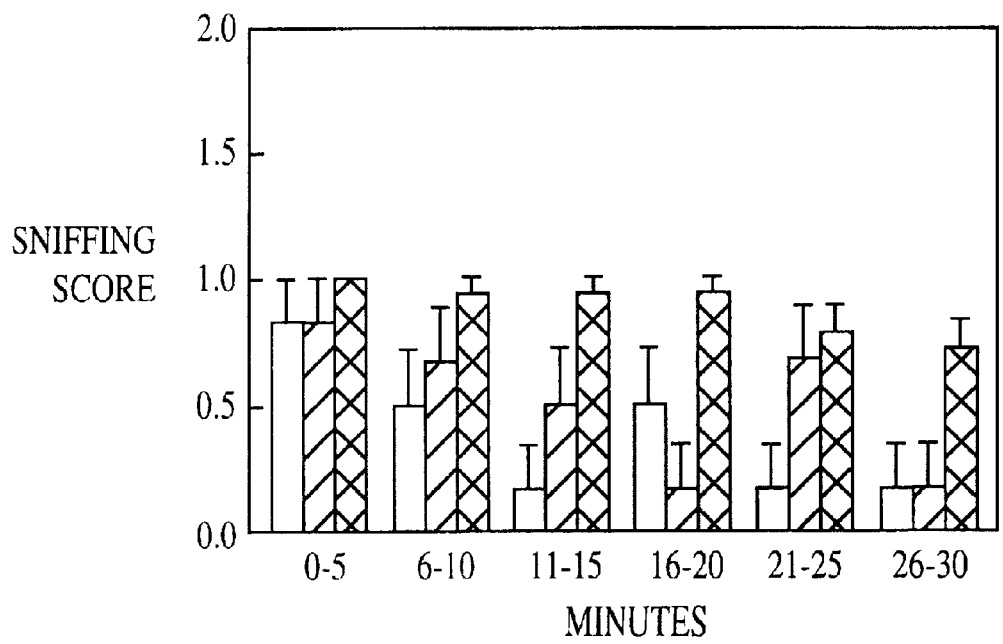
Figure 16C:
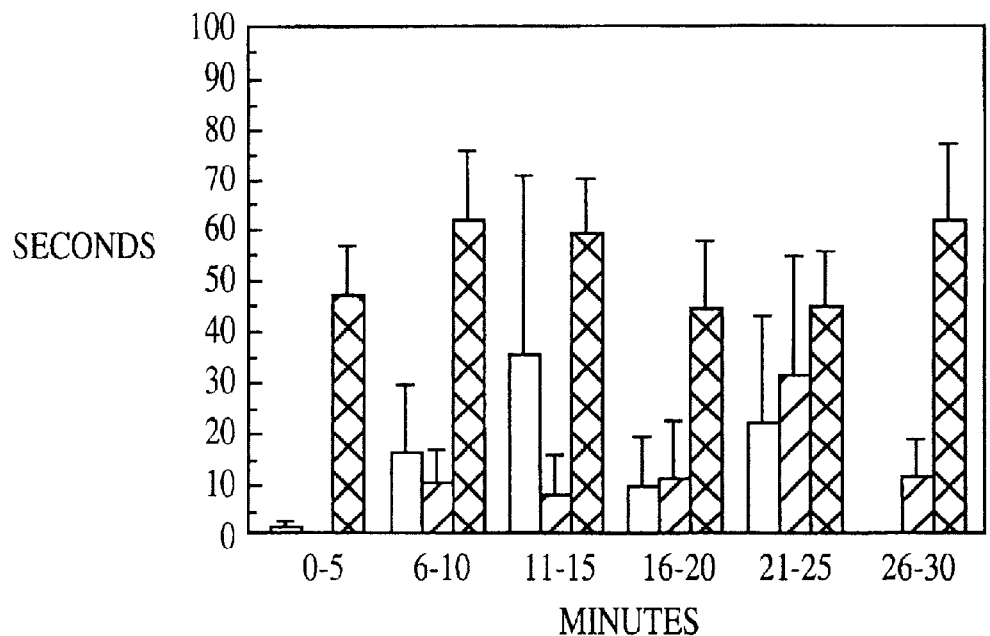
Figure 16D:
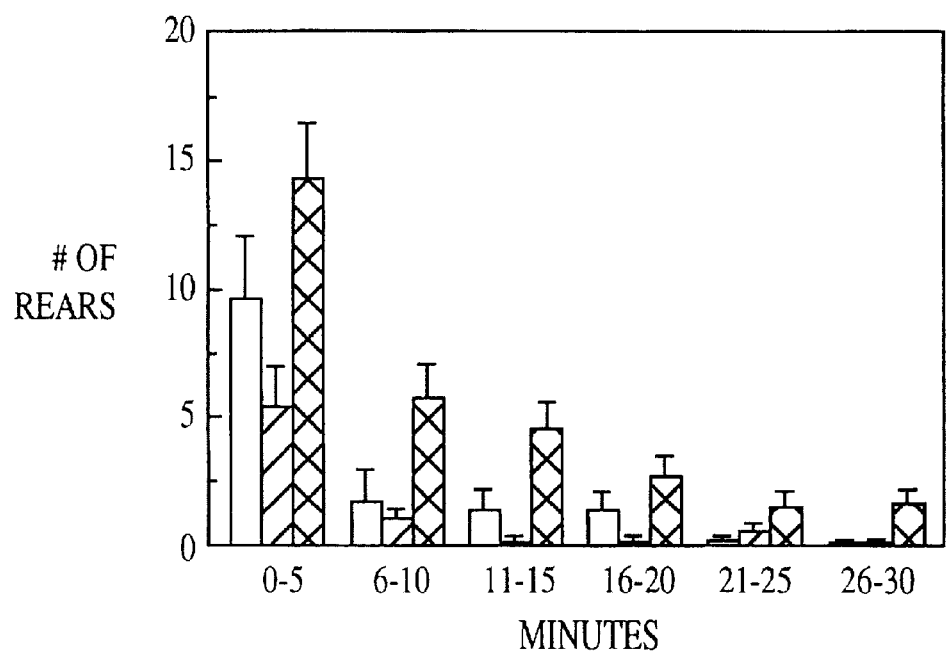

An open field test was conducted to examine the effects of CRIF on the behavior of test animals placed in a novel environment. Rats were placed in the center of a 15 inch diameter open-field 5 minutes after intracerebro-ventricular (icv) administration of CRIF, and their behavior was video-taped for 30 minutes. Analyses revealed a rapid habituation of behaviors over the 30 minute period in vehicle treated animals. In contrast, animals administered CRIF at a dose of 6 µg/kg exhibited significant increases in activity, sniffing, grooming behavior and rearing during this period compared with the vehicle treatment (FIGS. 16A, B, C and D). Little or no behavioral effect was observed in response to a lower dose of CRIF (0.6 µg/kg).

The anxiolytic properties of CRIF were tested using a light/dark box. The box is a plexiglass chamber divided into a lighted compartment connecting to an adjoining dark compartment. The test exploits the rodent's natural conflict between avoidance and exploration of lighted, open areas. Five minutes prior to testing, the animals were injected icv with CRIF or the vehicle alone. At the beginning of testing, each animal was placed in the center of the light compartment. Behavior was subsequently videotaped for 15 minutes. The behavior of the animals was scored by a trained observer who was unaware of the treatment status of each animal. The behaviors which were assessed were (A) initial latency in entering the dark compartment; (B) the number of compartment entries; and (C) total time spent in each compartment (FIGS. 17A, B and C). No significant difference was observed in the initial latency period prior to entry into the dark chamber. The number of crossings between the light and dark chambers was significantly increased in rats administered a high dose of CRIF ($p<0.05$). The total time spent in the light chamber was also significantly increased in these animals (i.e., those administered the high dose of CRIF) but was not affected in animals administered a low dose of CRIF or in vehicle treated animals ($p<0.05$).

The behavioral responses following icv administration indicate that this peptide has neurobehavioral effects in addition to its regulatory role in anterior pituitary ACTH and prolactin release. The increased exploratory behavior in the open field, as well as the increased activity in the light/dark box, suggest that CRIF may possess arousal properties. The increase in the time spent in the light compartment is suggestive of some anxiolytic properties in addition. Increased arousal is consistent with the increased grooming behavior in the open field induced by the peptide.

Grooming is a behavior which is activated by mild stress, and considered to be related to arousal. It can be induced in non-stressed animals by electrical stimulation or peptide infusion of the periventricular region of the hypothalamus. Although grooming behavior in response to environmental events is linked to HPA activation, the pattern of the response following different types of stressors suggests that the neuroendocrine and behavioral response may be activated simultaneously by independent mechanisms.

Figure 18:
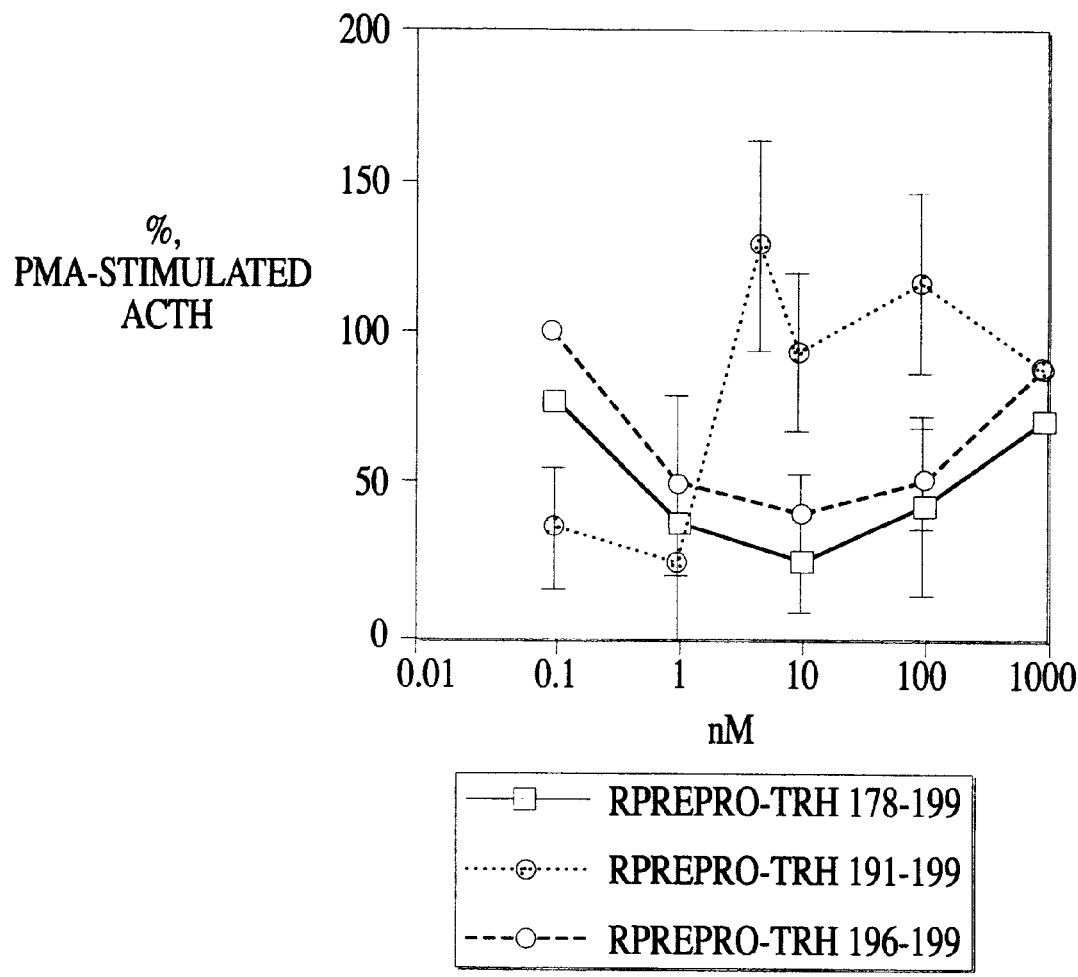
FIG. 18 is a graph depicting the fact that PMA-stimulated ACTH secretion is inhibited by peptides derived from rat prepro-TRH 178–199.
Figure 19:
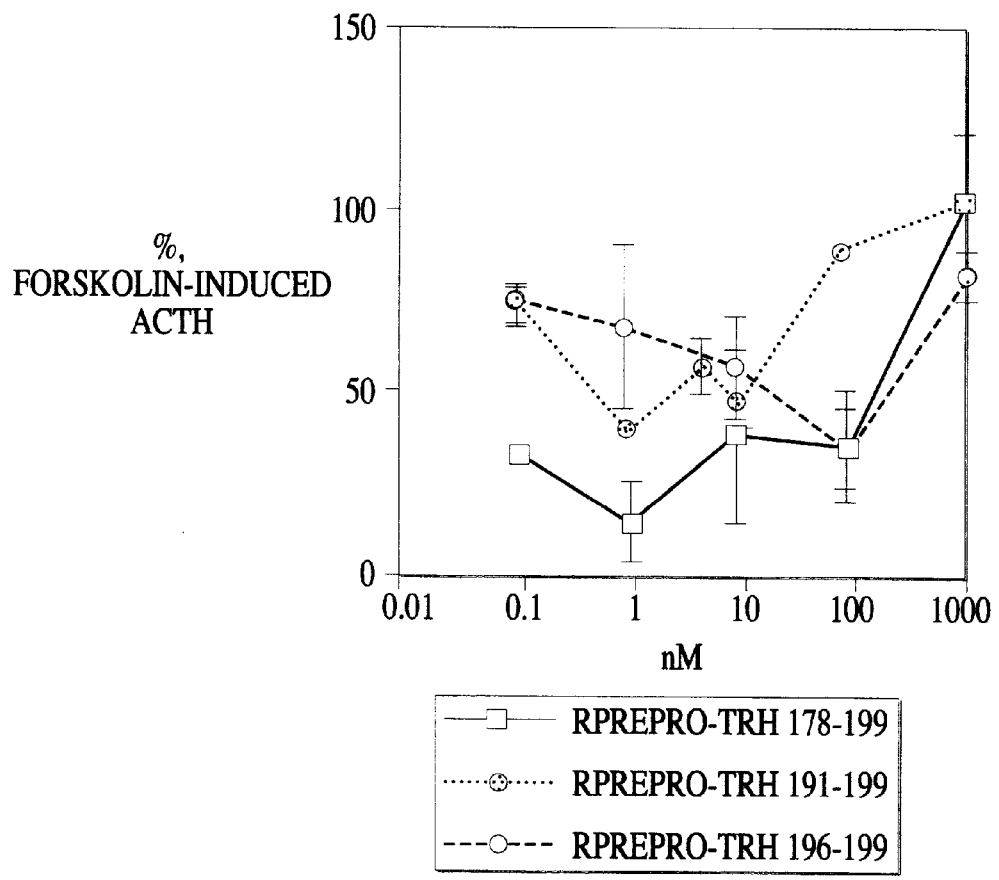
FIG. 19 is a graph and amino acid sequences [SEQ ID NOS:1, 6 and 5, resepctively], where the graph depicts the fact that forskolin-stimulated ACTH secretion is inhibited by peptides derived from prepro-TRH 178–199. The biological activity of small CRIF peptides was tested in vitro, using inhibition of ACTH release in At-20 cells as the bioassay. These peptides were tested in 2–7 independent experiments, where treatments were added in triplicate. Forskolin was used at a concentration of 20 µM, and PMA was used at a concentration of 100 nM.

Peptides having less than twenty two contiguous amino acids positioned within the prepro-TRH 178–199 molecule have CRIF activity CRIF peptides having either four contiguous amnino acids or nine contiguous amino acids positioned between the fourth and fifth TRH sequence in a rprepro-TRH polypeptide were prepared. These peptides are referred to herein as rprepro-TRH 196–199 (SEQ ID NO:5, having four contiguous amino acids) and rprepro-TRH 191–199 (SEQ ID NO:6, having nine contiguous amino acids). The amino acid sequence of these peptides is shown in FIG. 19. The CRIF activity of each of these peptides was assessed in vitro in a bioassay, wherein inhibition of ACTH release in At-20 cells was used as a measure of CRIF activity. Inhibition of PMA-stimulated ACTH secretion was assessed and the results are shown in FIG. 18. Full length CRIF (rprepro-TRH 178–199) was used as a positive control. The data establish that both rprepro-TRH 196–199 and rprepro-TRH 191–199 are capable of inhibiting ACTH secretion at levels which are comparable to those achieved using full length CRIF. Thus, CRIF peptides having less than twenty two contiguous amino acids have CRIF activity.

Figure 20:
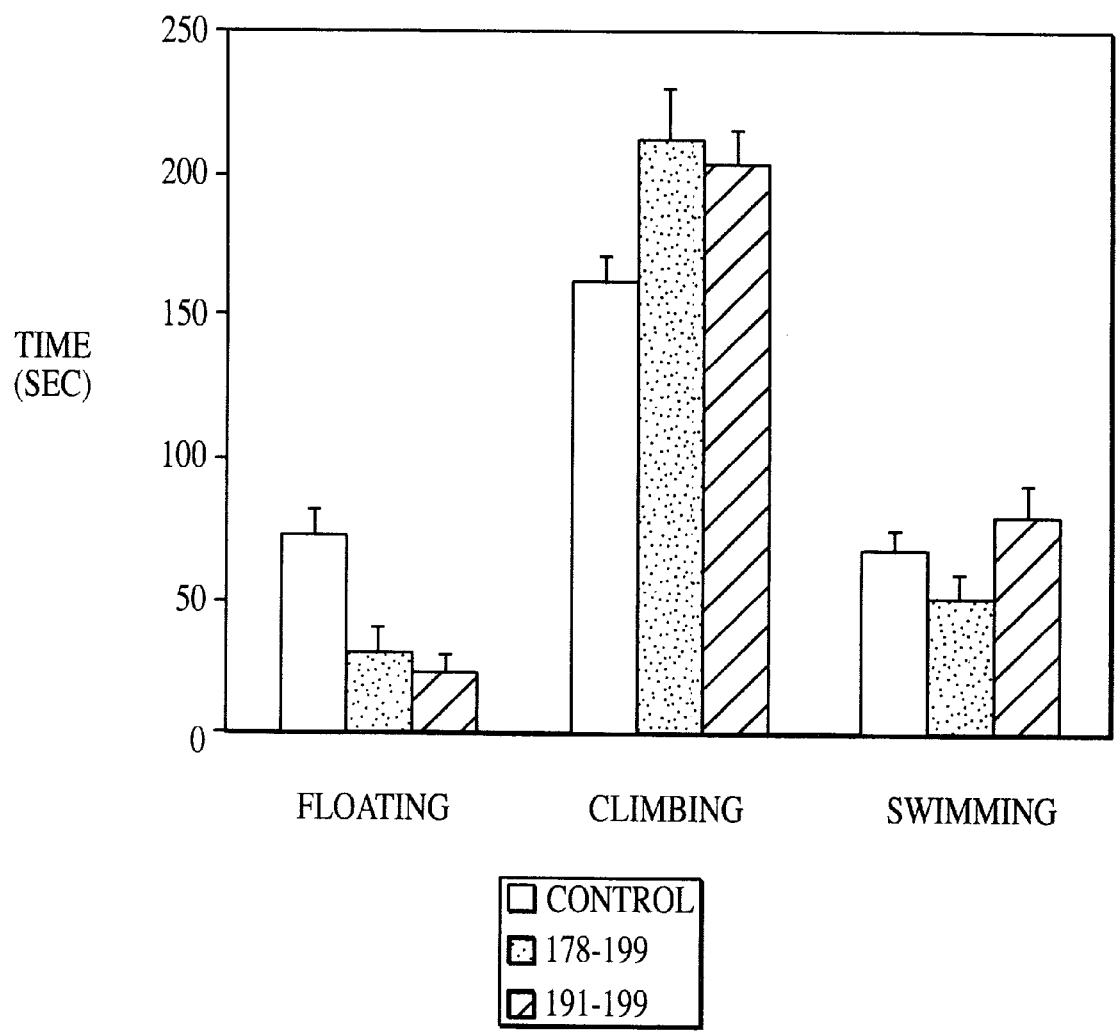
FIG. 20 is a graph which depicts the effects of central sub-acute administration of 6 mg/kg prepro-TRH 178–199 and 2.2 mg/kg prepro-TRH 191–199 on floating, climbing and swimming behavior in the forced swim test. Each value represents the mean +SEM of 7 (vehicle), 8 (prepro-TRH 178–199) and 8 (prepro-TRH191–199) rats.

In FIG. 20 there is shown data which establish that prepro-TRH 191–199 decreased immobility in the forced swim test when the peptide was administered to a rat icv. In this experiment, adult male Sprague-Dawley or F1 Brown Norway/Fisher344 rats were used in these experiments. Rats were implanted with cannulae into the lateral ventricle as described previously (McGivern, 1997, J. Neurosci. 17:4886–4894). For the stereotaxic surgery, animals were anesthetized (ketamine, 50 mg/kg/xylazine, 8 mg/kg) and positioned in a stereotaxic head fame. At the end of behavioral testing, placements will be verified by anesthetizing the animal with pentobarbital (45 mg/kg) and injecting 1 µl tryphan blue staining solution through the cannulae just prior to decapitation. Only data from animals with correct placement were included in the analysis.

At least 7 days after the stereotaxic surgery, animals were subjected to an initial 15 minute swim pretest, followed by a 5-minute swim test 24 hours later. Rats received two injections of sterile vehicle or prepro-TRH 178–199 (1.5, 3.0, 6.0 or 12.0 µg/kg; 0.6, 1.2., 2.3 and 4.6 nmol/kg) in 2–3 µg volume between the pretest and the test. 15 minutes after the initial (pre)-swim and 5 minutes before the test swim. In the case of prepro-TRH 191–199 administration, the C-terminal peptide was administered in this sub-acute fashion at 2.2 µg/kg (2.3 nmol/kg) dose, which is equivalent to 6 µg/kg prepro-TRH 178–199. Water was chosen instead of saline or artificial CSF for solubility reasons: the peptide dissolved much better in sterile, pyrogen-free water and animals tolerated this vehicle very well even after 14 days of daily administration. F344XBN rats were used. Prepro-TRH 191–199 had effects very similar to those of the full-length peptide. 2.2 µg/kg prepro-TRH 191–199 or the equimolar dose of 6 µg/kg prepro-TRH 178–199 administered in the sub-acute mode equally and significantly decreased floating ($F[2,29]=9.7$; $p<0.001$, FIG. 20) and increased climbing ($F[2,29]=6.0$; $p<0.01$), specifically climbing in the FST.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A substantially pure preparation of a CRIF peptide consisting of the sequence Leu-Met-Pro-Glu (SEQ ID NO:6).

2. A substantially pure preparation of a CRIF peptide consisting of from four to twenty one continuous amino acids contained within the amino acid sequence positioned between the fourth and fifth TRH sequence on a prepro-TRH protein, wherein said CRIF peptide contains the sequence Leu-Met-Pro-Glu (SEQ ID NO:6) and further consists of the sequence pGlu-His-Pro-Gly-Arg-Arg (SEQ ID NO:4) at the amino terminal portion of the peptide.

* * * * *

SEQUENCE LISTING

<160> NUMBER OF SEQ ID NOS: 9

<210> SEQ ID NO 1
<211> LENGTH: 22
<212> TYPE: PRT
<213> ORGANISM: Rattus sp.

<400> SEQUENCE: 1

Phe Ile Asp Pro Glu Leu Gln Arg Ser Trp Glu Glu Lys Glu Gly Glu
1               5                   10                  15

Gly Val Leu Met Pro Glu
            20

<210> SEQ ID NO 2
<211> LENGTH: 26
<212> TYPE: PRT
<213> ORGANISM: Rattus sp.

<400> SEQUENCE: 2

Leu Ala Asp Pro Lys Ala Gln Arg Ser Trp Glu Glu Glu Glu Glu Glu
1               5                   10                  15

Glu Glu Arg Glu Glu Asp Leu Met Pro Glu
            20                  25

<210> SEQ ID NO 3
<211> LENGTH: 16
<212> TYPE: PRT
<213> ORGANISM: Rattus sp.

<400> SEQUENCE: 3

Phe Ile Asp Pro Glu Leu Gln Arg Ser Trp Glu Glu Thr Glu Gly Glu
1               5                   10                  15

<210> SEQ ID NO 4
<211> LENGTH: 6
<212> TYPE: PRT
<213> ORGANISM: Rattus sp.

<400> SEQUENCE: 4

Gly His Pro Gly Arg Arg
1               5

<210> SEQ ID NO 5
<211> LENGTH: 9
<212> TYPE: PRT
<213> ORGANISM: Rattus sp.

<400> SEQUENCE: 5

Glu Gly Glu Gly Val Leu Met Pro Glu
1               5

<210> SEQ ID NO 6
<211> LENGTH: 4
<212> TYPE: PRT
<213> ORGANISM: Rattus sp.

<400> SEQUENCE: 6

Leu Met Pro Glu
1

<210> SEQ ID NO 7
<211> LENGTH: 84

```
<212> TYPE: DNA
<213> ORGANISM: Rattus sp.

<400> SEQUENCE: 7
caacatccag gccggaggtt catagatccc gagctccaaa gaagctggga agaaaaagag      60
ggagagggtg tcttaatgcc tgag                                            84

<210> SEQ ID NO 8
<211> LENGTH: 96
<212> TYPE: DNA
<213> ORGANISM: Homo sapiens

<400> SEQUENCE: 8
cagcacccag gcagaaggct ggcagatccc aaggctcaaa ggagctggga agaagaggag      60
gaggaggaag agagagagga agacctgatg cctgaa                               96

<210> SEQ ID NO 9
<211> LENGTH: 87
<212> TYPE: DNA
<213> ORGANISM: Mus sp.

<400> SEQUENCE: 9
cagcatccag gccggaggtt catagatcct gagctccaaa gaagctggga agaaacagag      60
ggagaggagg gtggcttaat gcctgag                                         87
```